(12) United States Patent
Lubinski et al.

(10) Patent No.: US 11,946,887 B2
(45) Date of Patent: Apr. 2, 2024

(54) DEVICE AND METHOD FOR ANALYZING A SUBSTANCE

(71) Applicant: DiaMonTech AG, Berlin (DE)

(72) Inventors: Thorsten Lubinski, Berlin (DE); Uwe Schriek, Berlin (DE)

(73) Assignee: DIAMONTECH AG, Berlin (DE)

(*) Notice: Subject to any disclaimer, the term of this patent is extended or adjusted under 35 U.S.C. 154(b) by 563 days.

(21) Appl. No.: 16/769,530

(22) PCT Filed: Dec. 4, 2018

(86) PCT No.: PCT/EP2018/083509
§ 371 (c)(1),
(2) Date: Jun. 3, 2020

(87) PCT Pub. No.: WO2019/110597
PCT Pub. Date: Jun. 13, 2019

(65) Prior Publication Data
US 2021/0164928 A1 Jun. 3, 2021

(30) Foreign Application Priority Data
Dec. 4, 2017 (WO) .................. PCT/EP2017/081398

(51) Int. Cl.
*G01N 29/24* (2006.01)
*G01N 25/18* (2006.01)
*G01N 33/49* (2006.01)

(52) U.S. Cl.
CPC ......... *G01N 25/18* (2013.01); *G01N 29/2418* (2013.01); *G01N 33/49* (2013.01)

(58) Field of Classification Search
CPC ............................. G01N 25/18; G01N 29/2418
See application file for complete search history.

(56) References Cited

U.S. PATENT DOCUMENTS 5,676,673 A * 10/1997 Ferre ..................... G01B 7/004
                                                         606/1
6,484,044 B1    11/2002 Lilienfeld-Toal
(Continued)

FOREIGN PATENT DOCUMENTS

EP          1048265 A1      11/2000
JP          H09133655    *   5/1997
(Continued)

OTHER PUBLICATIONS

Jonas Kottmann et al., *Mid-Infrared Fiber-Coupled Photoacoustic Sensor for Biomedical Applications*, Sensors 2013, 13, Jan. 2, 2013, doi: 10.3390/s130100535, ISSN 1424-8220, pp. 535-549.
(Continued)

*Primary Examiner* — Jamel E Williams
*Assistant Examiner* — Alex T Devito
(74) *Attorney, Agent, or Firm* — BURNS & LEVINSON LLP

(57) ABSTRACT

The invention relates to a device and a method for analyzing a substance (5), comprising an excitation transmitting device in the form of a laser device (3) for generating at least one electromagnetic excitation beam (8), a measuring body (1) having a detection region (4), which is adjacent to a measuring surface (2) of the measuring body (1) and has a pressure-dependent or temperature-dependent specific electrical resistance and/or generates electrical, in particular piezoelectric, voltage signals in the event of pressure or temperature changes, and comprising a device for analyzing the substance on the basis of detected signals.

26 Claims, 20 Drawing Sheets

(56) References Cited

U.S. PATENT DOCUMENTS

| | | |
|---|---|---|
| 2007/0015978 A1 | 1/2007 | Kanayama et al. |
| 2014/0142400 A1* | 5/2014 | Halaka ............... A61B 5/14532 600/316 |
| 2017/0146455 A1 | 5/2017 | Mäntele et al. |

FOREIGN PATENT DOCUMENTS

| | | |
|---|---|---|
| JP | 2001-25465 A | 1/2001 |
| JP | 2011-143259 A | 7/2011 |
| WO | WO 2017/097824 A1 | 6/2017 |

OTHER PUBLICATIONS

International Searching Authority/European Patent Office, International Search Report and Written Opinion of the International Searching Authority, Application No. PCT/EP2018/083509, dated Aug. 26, 2019, *with English translation of the Search Report*, 25 pages.

Japan Patent Office, Notice of Reasons for Refusal, Application No. 2020-530510, dated May 26, 2022, 68 pages (*with machine translation*).

European Patent Office; Examination Report; Application No. 18815162. 5, dated Oct. 20, 2022, 4 pages (in German).

\* cited by examiner

DEVICE AND METHOD FOR ANALYZING A SUBSTANCE

CROSS-REFERENCE TO RELATED APPLICATIONS

This application is the national phase entry of International Patent Application No. PCT/EP2018/083509 filed on Dec. 4, 2018, and claims the benefit of International Patent Application No. PCT/EP2017/081398 filed Dec. 4, 2017, the disclosures of which are incorporated herein by reference in their entirety.

The present patent application relates to a device and a method for analysing a substance, taking particular, if not exclusive, consideration of detection methods that make use of a piezo-effect. The device described here and the method described here can be used, for example, for the analysis of animal or human tissue, bodily fluids and in one embodiment, for measuring glucose or blood sugar.

Known methods for analysing a substance, in particular for measuring blood sugar, are described, for example, in the following documents:

Guo et al.: "Noninvasive glucose detection in human skin using wavelength modulated differential laser photothermal radiometry", Biomedical Optics Express, Vol. 3, 2012, No. 11, Uemura et al.: "Non-invasive blood glucose measurement by Fourier transform infrared spectroscopic analysis through the mucous membrane of the lip: application of a chalcogenide optical fiber System", Front Med Biol Eng. 1999; 9(2): 137-153, Farahi et al.: "Pump probe photothermal spectroscopy using quantum cascade lasers", J. Phys. D. Appl. Phys. 45 (2012) and M. Fujinami et al.: "Highly sensitive detection of molecules at the liquid/liquid interface using total internal reflection-optical beam deflection based on photothermal spectroscopy", Rev. Sci. Instrum., Vol. 74, Number 1 (2003).

(1) von Lilienfeld-Toal, H. Weidenmüller, M. Xhelaj, A. Mántele, W. A Novel Approach to Non-Invasive Glucose Measurement by Mid-Infrared Spectroscopy: The Combination of Quantum Cascade Lasers (QCL) and Photoacoustic Detection *Vibrational Spectroscopy*, 38:209-215, 2005.

(2) Pleitez, M. von Lilienfeld-Toal, H. Mántele W. Infrared spectroscopic analysis of human interstitial fluid in vitro and in vivo using FT-IR spectroscopy and pulsed quantum Cascade lasers (QCL): Establishing a new approach to non-invasive glucose measurement *Spectrochimica Acta. Part A, Molecular and Biomolecular spectroscopy*, 85:61-65, 2012

(3) Pleitez, M. et al. In Vivo noninvasive Monitoring of glucose concentration in Human Epidermis by Mid-Infrared Pulsed Photoacoustic Spectroscopy *Analytical Chemistry*, 85:1013-1020, 2013.

(4) Pleitez, M. Lieblein, T. Bauer, A. Hertzberg, O. of Lilienfeld-Toal, H. Mántele, W. Windowless ultrasound photocoutic cell for in vivo mid-IR spectroscopy of human epidermis: Low interference by changes of air pressure, temperature, and humidity caused by skin contact opens the possibility for non-invasive monitoring of glucose in the interstitial fluid *Review of Scientific instruments* 84, 2013

(5) M. A. Pleitez Rafael, O. Hertzberg, A. Bauer, M. Seeger, T. Lieblein, H. von Lilienfeld-Toal, and W. Mántele. Photothermal deflectometry enhanced by total internal reflection enables non-invasive glucose monitoring in human epidermis. *The Analyst*, November 2014.

The object of the invention is to specify a device and a method which can be used to analyse a substance, in particular an animal or human tissue or a component or ingredient of the tissue, in a particularly simple and cost-effective manner. One aspect of the invention also involves the achievement of a small size of the device.

This object is achieved, inter alia, by a device having the features in accordance with claim 1. Embodiments of the device are specified in sub-claims. In addition, the invention relates to a method in accordance with the independent method claim with corresponding embodiments according to the sub-claim(s) dependent thereon.

Reference is made to the German patent specification DE 10 2014 108 424 B3, the content of which is specifically referred to here and on which the content of this application is based; the entire content of the German patent specification DE 10 2014 108 424 B3 is therefore to be regarded through this explicit reference as also being part of the disclosure content of this application ("incorporation by reference" for all details of the disclosure therein). In particular, this reference relates to all of the features mentioned in the granted patent claims. In addition, the reference also relates in particular to details of the excitation light beam mentioned there, for example to the numerical values of pulse frequencies and wavelengths (wavelength ranges) mentioned there, and also to the details of the measurement of glucose content in the interstitial fluid.

In addition to the subject matter of the claims and exemplary embodiments explicitly mentioned at the time of filing, this patent application also refers to other aspects listed at the end of the present description. These aspects can be combined individually or in groups, in each case with features of the claims cited at the time of filing. These aspects also constitute independent inventions, whether taken in isolation or combined with one another or with the claimed subject matter of this application. The applicant reserves the right to make these inventions the subject of claims at a later date. This may occur as part of this application or within the context of subsequent sub-applications, continuation applications (U.S.), continuation-in-part applications (U.S.), or follow-up applications that claim priority of this application.

In connection with the following statements the terms "light" or "laser light" mean electromagnetic waves or electromagnetic radiation in the visible range, the near, medium and far infrared range, and in the UV range.

One possible aspect of the method presented here is the focusing of the measurement of the response signal on selected depth ranges below the (spacing intervals of the) material surface. The parameter d has the greatest influence on the depth range measured using the method. It is defined as $d=\sqrt{D/(\pi*f)}$, where D is the thermal diffusivity of the sample (e.g. here, skin) and f is the modulation frequency of the excitation beam. Literature on the thermal diffusivity of skin:

U. Werner, K. Giese, B. Sennheiser, K. Plamann, and K. Kólmel, "Measurement of the thermal diffusivity of human epidermis by studying thermal wave propagation," Phys. Med. Biol. 37(1), 21-35 (1992).

A. M. Stoll, heat Transfer in Biotechnology, Vol 4 of advances in heat Transfer, J. P. Hartnett and T. Irvin, eds. (New York, Academic, 1967), p 117.

In order to eliminate response signals from the topmost layers of the substance for the purpose of improving the quality of the measurement, in one embodiment changes in the measurement values compared to previous measurements can be used if the measurements in the topmost layers change to a lesser extent or more slowly compared to other, deeper layers. This can be the case in an embodiment in measurements on human skin, where the topmost layers of the skin are in practice not subject to an exchange with the lower layers and therefore physiological parameters do not vary very much. The temporal derivative of measured values can also be used for response signals to exclude the signals from the topmost skin layers. In this way, the measurement or at least the evaluation can be limited to or focused on the interstitial fluid in the skin.

For this purpose, a measurement can include the acquisition of response signals for spectra that are acquired multiple times with different modulation frequencies of the excitation light source, combining the results for different modulation frequencies, for example by differentiating or forming the quotient of the measurement values of response signals for the same wavelengths and different modulation sequences. To perform such a measurement a device with an appropriate control device for the excitation beam and an evaluation device for the spectra of response signals should also be provided.

The following text first deals with the subject matter of the claims listed at the time of filing.

The object is achieved with the features of the invention according to patent claim 1 by a device for analysing a substance having:
- a measuring body having a measuring surface which is to be brought at least partially into contact with the substance for the measurement,
- an excitation beam source, in particular a laser device, more particularly with a quantum cascade laser (QCL), a tunable QCL, and/or a laser array, preferably an array of QCLs, for generating one or more excitation beams of different wavelengths, preferably in the infrared spectral range, which is directed at the substance by passing through the measuring surface, and
- a detection device, which comprises the following:
  - a detection region which is part of the measuring body and arranged in particular adjacent or directly adjacent to the measuring surface, and the material of which has electrical properties that vary as a function of a change in pressure or temperature, and
  - electrodes that can be used to detect electrical signals that represent the electrical properties specified.

In this case, the specified properties of the region can be, in particular, properties of the material of the region.

The preferred approach is to use such a device to analyse a substance in which the electrical property, which changes depending on the pressure or temperature,
- gives rise to piezoelectric signals on the electrodes as a function of the pressure change and/or the temperature change, or
- is formed by a specific electrical resistance, which varies according to the temperature,
- wherein the device also comprises an electrical contact device which comprises the said electrodes, which are electrically conductively connected to the detection region of the measuring body for detecting the electrical resistance and/or the piezoelectric signals.

In the case of the detection of piezoelectric signals, the electrical property that varies as a function of the pressure or temperature can be referred to as "polarization". Other electrical properties that vary as a function of pressure and/or temperature and can be exploited for the purposes of the invention are equally possible, such as the dielectric constant.

In this context, the excitation beam shall be understood to mean a light beam, a laser beam or even a multiplicity of substantially parallel laser beams which are emitted sequentially or simultaneously by the excitation beam source, in particular a laser device or individual laser elements of an excitation beam source, in particular a laser device, to the substance to be analysed. The coherence of the excitation beam is not required, so that even non-coherent or only partially coherent radiation can also be used. In this respect, in addition to laser devices other light sources, such as LEDs/semiconductor diodes or others, which allow the selection of wavelengths or wavelength ranges, can also be used as beam sources. When using a more broadband light source for the excitation beam, wavelength filters, such as tuneable filters, can also be used to selectively generate excitation beams for different wavelengths or wavelength ranges.

For different applications, it may be useful to select an excitation beam in the mid-infrared range. For example, it is also possible to select as the light source a laser which operates using the OPA (optical parametric amplification) or NOPA (non-collinear optical parametric amplification) or OPG (optical parametric generation) methods, and allows the generation of different wavelengths using such a method.

It is also possible to use a so-called optical parametric oscillator (OPO) in an optical resonator that has an optically nonlinear crystal, for example beta-barium borate. Due to the non-linear three-wave interaction, the crystal generates, inter alia, radiation of a transformed wavelength from the injected pump wave. In this way, as with the above-mentioned OPA/NOPA methods or arrangements, for example, from radiation in the near infrared wavelength range a radiation in the mid-infrared range can be obtained, which can be used for the spectroscopic procedures described in this application.

The detection region of the measuring body refers to a spatial region or section of the measuring body that exhibits the above properties by having a temperature- or pressure-dependent specific electrical resistance and/or by generating electrical, in particular piezoelectric, voltage signals under the application of pressure or temperature changes. This is achieved by the material selection and optionally also by further configuration, for example processing, of the material of which the detection region consists.

It may be the case that the regions of the measuring body adjacent to the detection region differ from the material of the detection region in this respect, in particular in terms of the material of which they consist. However, it may also be provided that the regions of the measuring body adjacent to the detection region, as well as the detection region itself, have a temperature- or pressure-dependent specific electrical resistance and/or generate electrical, in particular piezoelectric, voltage signals in the event of pressure or temperature changes. The detection region can be separated from other regions of the measuring body by electrodes and/or separation regions, wherein the separation regions can be made of a material that is considerably softer, more elastic or more flexible than the material of the detection region, so that the material of the separation regions conducts a pressure or temperature increase less well than the material of the detection region.

In particular, the measuring body may also be formed by a first part and a second part of the measuring body implemented as a sensor layer, wherein the sensor layer may have a different composition than the first part of the measuring body and, in particular, can be at least partially composed of a piezoelectric material. The sensor layer can be applied, in particular adhesively bonded, to the first part of the measuring body in the region of the measuring surface. The sensor layer can also be made of a material that has a greater dependence of the refractive index on pressure or temperature than the first part of the measuring body. The first part of the measuring body can be transparent to the excitation beam/excitation beams, and may consist of silicon, for example. If the sensor layer for the excitation beam(s) is not transparent or is less transparent than the first part of the measuring body, then the sensor layer can have a slot to allow the passage of the excitation beam(s). In the slot, for example, a lens may also be provided to focus the excitation beam(s) onto a point in the substance to be analysed.

An optical waveguide that ends in, on or in front of, the measuring surface may also be provided inside the measuring body to guide the excitation beam(s). The optical waveguide can be integrated into a substrate of the measuring body and manufactured in SOI technology. The optical waveguide can pass through the detection region or can also be guided past it. The optical waveguide can be composed of a material that has no or only a minimal dependence of the refractive index on a mechanical pressure, in order to minimize the influence of piezoelectric pressure generation on the excitation beam. The optical waveguide material can also be mechanically spaced apart from the piezoelectric material provided in the detection region or be mechanically decoupled from it by a flexible, in particular elastic material layer or a gas layer.

The object is alternatively achieved with the features of the invention according to patent claim 2 by a device for analysing a substance having:

a measuring body having a measuring surface which is to be brought at least partially into contact with the substance for the measurement, an excitation beam source, in particular a laser device, more particularly with a quantum cascade laser (QCL), a tuneable QCL, and/or a laser array, preferably an array of QCLs, preferably in the infrared spectral range, for generating an excitation beam of different selectable wavelengths, which is directed at the material while passing through the measuring surface, and with at least one detection device that is arranged adjacent to and/or directly adjoining the measuring surface, the detection device having a contact device with at least two electrodes for detecting piezoelectric signals, said electrodes being located opposite each other on different sides of a detection region. In the detection region, a material is arranged that changes its electrical resistance or generates an electrical signal as a function of temperature and/or pressure changes, in particular due to a piezoelectric effect.

The excitation source, in particular the laser device, sends an excitation beam into the substance to be analysed, which, for example, sweeps through certain wave numbers/wavelengths or emits a multiplicity of excitation beams with specific fixed wave numbers, sequentially or simultaneously, both in the case of the subject matter of claim 1 and in the case of the subject matter of claim 2. In this case, the wavelength selection can also be carried out later by means of filters in the light path behind the excitation beam source.

When using an array, the laser array may have simple fixed-wavelength lasers. At certain wavelengths, the beam is absorbed depending on of the material of the substance to be analysed, so that energy is released which is transported at least partly in the form of a thermal wave to the surface of the material, and then into the measuring body and there also to the detection region. The excitation beam is advantageously intensity-modulated, wherein the use of different, even a plurality of, modulation sequences is possible. It is also possible to form laser pulses that contain a multiplicity of modulation frequencies in the Fourier-transform domain. The pulsed heating of the material in the detection region causes a change in resistance and/or an electrical voltage signal to be generated and/or other parameter changes, such as a change in the refractive index. By means of the electrodes of the contact device and their supply cables the first two electrical phenomena mentioned can be connected to a measuring device that measures voltages and/or electrical resistances and which evaluates these changes and assigns them a temperature increase and/or an absorption intensity of the excitation beam in the substance. The absorption intensity can thus be measured as an absorption spectrum as a function of the wave numbers/frequencies of the excitation beam that are traversed.

The detection region is advantageously located adjacent to the measuring surface, i.e. it is arranged either directly adjacent to it or at a distance from the measuring surface, wherein this distance should be small (for example, less than 10 microns or less than 100 microns, in each case measured at the smallest distance between the detection region and the measuring surface). For example, the detection device may also comprise a plate or a body that is joined together with another part of the measuring body as part of the measuring body, or else a coating of a part of the measuring body in the region of the measuring surface.

In particular in the case of a pressure change being detected, for example when using a piezo-sensitive material/piezo-sensor, the detection device can also be used to detect a response signal in the form of a sound wave, which is generated by the absorption of the excitation beam in the substance to be analysed and travels to the measuring surface and to the detection region at a known speed (in human tissue, approx. 1500 m/s). By means of an evaluation device connected to a modulation device for the excitation beam, due to the good temporal resolution of the measurement of the response signals, a phase shift between the modulation of the excitation beam and the response signal can be measured, thereby determining the depth in the tissue in which the absorption took place. Since the signals are often a superposition of different response signals from different tissue layers, different measurements can be carried out at different modulation frequencies and the response signals at different modulation frequencies can be correlated to cancel out and eliminate, in particular, signals from upper tissue layers, as these are particularly susceptible to errors due to contamination by dirt and dead skin cells.

It should be noted that in the present disclosure, the same term "response signal" is used in several ways. On the one hand, it can describe the physical response to the excitation by the excitation beam, i.e. such as a sound wave, a temperature increase or the like. On the other hand, it can also refer to a (typically electrical) signal that represents this physical response, i.e. such as a voltage or a current flow measured by the electrodes. For the sake of simplicity and coherence of the presentation, the same term "response signal" is used throughout, it being clear from the context without further explanation whether it refers to the physical response (for example, a pressure wave), a physical consequence of that physical response (for example, a compression of a piezoelectric material), or the associated measurement signal (for example, the voltage generated by the piezoelectric material).

Instead of different modulation frequencies, signals with a steep rise (ideally so-called Dirac pulses) can also be formed, which represent a mixture of many modulation frequencies and allow an analysis of different modulation frequencies by means of a Fourier analysis.

An implementation of the device may provide that at least two electrodes, in particular along a surface normal of the measuring surface, are located one behind another at different distances from the measuring surface, or are spaced apart from each other on different sides of the detection region in a direction perpendicular to the surface normal.

The measuring surface can be flat or curved. In the curved case, the surface normal is understood to mean a normal to the measuring surface at a point, in particular at a location where the excitation beam passes through the measuring surface.

At least two electrodes should be arranged such that they completely or partially surround the detection region, or that the detection region is located completely or partially between the two electrodes. The electrodes can be distributed in different geometric locations on different sides of the detection region, in particular distributed around the detection region.

A further implementation of the device can provide for the excitation beam to pass through the measuring body, in particular through the detection region, wherein an optical waveguide is arranged in or on the measuring body, in particular to guide the excitation beam, and also in particular, the optical waveguide is integrated into the measuring body.

The excitation beam thus travels through the measuring body, for example directly through the material of the measuring body or through an optical waveguide arranged therein, and through the detection region or past the detection region to the point of the substance to be analysed, which absorbs the excitation radiation and emits the heat radiation.

An optical waveguide integrated into the material of the measuring body and/or into the material of the detection region can be used as an optical waveguide for guiding the excitation beam. Such optical waveguides can be applied, for example, by an epitaxial method or by selective doping of wafer material in or onto a wafer. However, a fibre-optic cable can be inserted into the measuring body or else at least partially applied to this on the outside.

It may also be provided that the excitation beam passes through the measuring surface in a region which is directly adjacent to and/or adjoins the detection region.

A further implementation of the device may provide for a modulation device to modulate the intensity of the excitation beam. In this case, different types of modulation are possible, using a mechanical chopper as well as using a controllable shutter or deflection mirror device, or a body/layer the transmission of which is controllable. In addition, modulation can also be achieved directly by the activation of the excitation light source/laser light source. A measurement may then include the acquisition of spectra at one or more modulation frequencies, wherein measurements at different modulation frequencies can be correlated with each other to obtain depth information and/or eliminate measurement data from specific depth ranges of the sample/substance to be analysed. In particular, measurement data originating from the surface of the substance can therefore be eliminated. These are measurement data and thermal waves that result from the absorption of the excitation light beam at the surface of the substance and which may be caused by impurities or anomalies on the surface of the substance to be analysed. One example of this, in the analysis of the skin of a patient, are the uppermost layers which consist partly of dead cells, which have an uninformative composition and/or provide false information. This is particularly the case if biologically active substances, active metabolism or metabolic products or similar are to be detected in the skin.

In the following, various geometric electrode configurations are presented and their advantages are discussed.

To this end it can be provided, for example, that at least two, in particular at least three or four, more particularly at least 6, more particularly at least 8 electrodes are arranged one behind another at different distances from the measuring surface, or spaced apart from each other in a direction perpendicular to a surface normal of the measuring surface.

At least one or more of the electrodes is/are arranged on each side of the detection region. This means that different pairs of electrodes are available that can be used to measure an electrical resistance or voltage.

An electronic device is provided for this purpose, which is connected to a plurality of or all electrodes via supply cables. The electronic device has a control device and, in particular, an evaluation device that causes/cause the acquisition and evaluation of electrical resistances or voltages between different selectable electrodes sequentially or simultaneously.

To this end, different pairs or all pairs of electrodes can be tentatively selected. The selected electrodes of a pair of electrodes for a tentative measurement should each have at least part of the detection region between them. Measurements from individual electrode pairs can be compared with each other and evaluated. Evaluation parameters can be, for example, the signal strength or the magnitude of the signal changes, or a signal-to-noise ratio or other parameter. In addition to the integration of the electrodes into the measuring body, another case that should also be comprised is that in which a plurality of electrodes are applied in a staggered pattern over the surface of the measuring body/measuring surface by adhesion, or have been incorporated or evaporated thereon.

It may also be provided that at least two, in particular at least three or four, in particular at least 6, in particular at least 8 electrodes are arranged in the direction of a surface normal of the measuring surface, or perpendicular to it, or in a direction between 0 and 90 degrees to the surface normal, one behind another at different distances from the detection region, in particular at different distances from the centre of the detection region. The detection region in this case can be defined, for example, by a spatial region of the measuring body consisting of a particular material. The detection region can also be defined by the overall arrangement as a region of the measuring body located above the entry point of the excitation beam into the material to be analysed.

In addition, the detection region can also be defined by the sum of the spatial points at which an electrical signal is potentially detectable by the available electrodes.

A further implementation can provide that at least two, in particular at least three or four, more particularly at least 6, more particularly at least 8 electrodes are arranged in an annular or spherical shell-shaped region around the detection region and at least partially opposite one another on different sides of the detection region, wherein different electrodes have essentially the same distance from the centre of the detection region or different distances from the centre of the detection region. This is intended to also include the case of electrodes distributed over the surface of the measuring body.

By means of the above electrode distribution and, for example, measuring at multiple pairs of electrodes, the electrode pair(s) that is or are most suitable for measurement can be selected and used.

As a suitable measure of the measurement quality when selecting the electrode pairs, either a signal strength or a signal dynamic range or a noise level or a signal/noise ratio can be used, for example.

It may also be provided that one or more or all of the electrodes of the contact device are designed to be disc-shaped or plate-shaped, annular, annular disc-shaped, in the form of a rectangular or polygonal frame with an opening, cap-shaped or rod-shaped.

An implementation of the device can provide that one or more or all of the electrodes of the contact device are arranged on one surface of the measuring body or the detector device and, in particular, are attached by means of a joining method, in particular by adhesive bonding or welding. They can also be applied by vapour deposition or coating. The measuring body can be made of a single homogeneous material, or in the detection region it may consist of a special material that differs from the material of the other regions of the measuring body.

The electrodes are usually made of metal for all embodiments, in any event from a material with good electrical conductivity. They can also be made of an electrically conductive plastic or a conductively filled material.

A further implementation of the device can provide that one or more or all of the electrodes of the contact device are arranged on the inner side or the outer side of the measuring body in one or more slots, such as bored holes, recesses or grooves of the measuring body, in particular being inserted, cast into, incorporated by injection moulding or by an additive manufacturing method (3D printing). These variants allow the insertion of electrodes into a measuring body in a technically simple way.

Electrodes can also be created in the measuring body by making regions of the material of the measuring body electrically conductive by irradiation or by bombardment with particles. This is possible, for example, in plastics in which high-energy radiation partially destroys carbon molecules and forms carbon accumulations that are conductive.

In addition, it can be provided that the measuring body is formed as a flat body, in particular as a plane-parallel body in the form of a plate, wherein in particular the thickness perpendicular to the measuring surface is less than 50% of the smallest extension of the measuring body in a direction extending in the measuring surface, in particular, less than 25%, more particularly less than 10%.

This design variant of the measuring body can be used for different detection methods of the thermal response signals and is not limited in principle to the detection method based on a piezo-effect. It can also be used in the measuring method with a measurement beam reflected at the measuring surface and a detector for detecting its deflection, and allows a significant reduction in the dimensions of the measuring body in the direction perpendicular to the measuring surface. Regardless of the measurement method, for example by using the piezo-effect or by measuring the deflection of a reflected beam, the measuring body formed as a flat body can have a layer in the region of the measuring surface, which layer in the case of the piezo-measurement method can consist of a piezoelectric material and in the case of detection by measuring the deflection of a reflected measurement beam, of a material in which the refractive index changes more strongly as a function of temperature than in the material of the other regions of the measuring body.

A further implementation of the device may provide that the measuring body has a mirror device for reflecting the excitation beam irradiated by the excitation beam source, in particular the laser device, or carries such a mirror device.

In the case of a very flat measuring body, the excitation beam can be irradiated from the flat side of the measuring body. The excitation beam then propagates from the excitation beam source, initially essentially parallel to the measuring surface within the measuring body or parallel to the boundary surfaces of the measuring body, and is then deflected towards the measuring surface.

Instead of reflecting the excitation beam, it can also be diffracted towards the measuring surface by means of suitable material design of the measuring body. The flat body can also have optical focussing elements for the excitation beam or be connected to such elements, for example, one or more lenses.

It can also be provided that the excitation beam is irradiated into the measuring body parallel to the measuring surface or at an angle of less than 30 degrees, in particular less than 20 degrees, more particularly less than 10 degrees or less than 5 degrees to the measuring surface, and that the excitation beam is diverted or deflected towards the measuring surface and passes through it.

Integrated into or directly connected to the measuring body, especially when a flat body is used, a focussing device can be provided, e.g. in the form of a diffracting element/lens, which focusses the excitation beam onto the measuring surface and the substance surface of the substance to be analysed.

It may also be provided that the excitation beam passes through the material of the measuring body.

It may also be provided that the measuring body has at least one slot, in particular a bored hole, which is penetrated by the excitation beam, wherein the slot and/or bored hole extends, in particular, from the measuring surface into the measuring body, or wherein the recess or slot and/or bored hole passes through the entire measuring body from a boundary surface opposite the measuring surface of the measuring body to reach the measuring surface. The recess can extend as a channel or bored hole with its longitudinal axis also at least partially in the direction of the excitation beam parallel to the measuring surface. If a sensor layer is provided, the slot, recess and/or bored hole can extend into the measuring body from the boundary surface of the sensor layer opposite the measuring surface, so that the sensor layer itself is not penetrated by the slot.

In this case, the measuring body can have a hollow channel/bored hole/recess for the excitation beam, so that the excitation beam does not penetrate the material of the measuring body, even though the excitation beam passes through the measuring body and the measuring surface to the substance to be analysed.

It may also be provided that the measuring body has a first part that has a continuous channel for the excitation beam, and that the measuring body on its underside on the first part has a sensor layer, which is either continuous without a recess or with a continuation of the recess of the first part. If the sensor layer is thinner than 200 microns, in particular thinner than 100 microns, the excitation beam can pass through it—even if it is an infrared beam—without too much absorption, and a recess, bored hole or channel in the sensor layer is not necessary. The sensor layer of the measuring body can consist of a material that has piezoelectric properties and forms a detection region according to the invention. The sensor layer can also consist of a material in which a change in temperature and/or pressure causes a change in the refractive index, so that this change can also be detected as a response signal, for example by detecting the angle of reflection of a detection beam that is reflected in the sensor layer. For example, the first part of the measuring body can then consist of a material such as quartz or sapphire, which is transmissive in the visible range and for a detection beam, but is less transmissive or opaque in the infrared spectral range.

A further implementation of the device can provide that in or on the measuring body, in particular in the detection device, or directly adjacent to and in thermal contact with it, at least one heat sink is arranged in the form of a body, the specific thermal capacity and/or specific thermal conductivity of which is greater than the specific thermal capacity and/or specific thermal conductivity of the material from which the measuring body is composed, or which is designed as a Peltier element.

Instead of a heat sink in the form of a body, the specific thermal capacity and/or thermal conductivity of which is greater than the specific thermal capacity and/or specific thermal conductivity of the material from which the measuring body is made, an active or passive cooling element, in particular a Peltier cooling element for adjusting a temperature gradient, may also be provided. The temperature gradient or the absolute temperature can also be controlled by means of the Peltier element using a closed-loop control device.

With heat sinks of this kind, for example in the form of metal or crystal bodies or actively operated Peltier elements, the appropriate thermal properties of the measuring body with regard to the thermal diffusivity can be achieved, which are necessary to ensure that both the temperature change builds up sufficiently in the detection region with the modulation frequency, and that the heat is transported away sufficiently quickly. Of course, this depends primarily on the material of the measuring body/detection device, but it can be influenced by the appropriate addition of one or more heat sinks. For example, these can be at least partially arranged around the detection region or else be provided on one side of the detection region.

A further implementation of the device can provide that in or on the measuring body, in particular in the detection device or directly adjacent thereto and in thermal contact therewith, at least one thermal barrier is arranged in the form of a body, the specific thermal capacity and/or specific thermal conductivity of which is less than the specific thermal capacity and/or specific thermal conductivity of the material from which the measuring body is made.

With thermal barriers of this kind, alone or also in combination with heat sinks, the appropriate thermal properties of the measuring body with regard to the thermal diffusivity can be achieved, which are necessary to ensure that both the temperature change is built up sufficiently in the detection region with the modulation frequency, and that the heat is also transported away corresponding to the modulation frequency sufficiently quickly. This can be influenced by suitable addition of one or more thermal barriers. For example, these can be at least partially arranged around the detection region or else be provided on one side of the detection region. Thermal barriers can be implemented, for example, by thermally insulating plastic elements. For example, one or more heat sinks can be provided on the first side of the detection region and one or more thermal barriers on a second side of the detection region opposite the first, to generate a temperature gradient and to control the direction of the heat transport.

It may be provided that the detection device and/or the measuring body consists at least partially of a piezoelectric material, in particular a piezoelectric ceramic, in particular a PZT ceramic, more particularly a sintered ceramic, or a single-crystalline piezoelectric material, in particular quartz, tourmaline, lithium niobate, gallium orthophosphate, berlinite, Seignette salt, ferroelectrics such as barium titanate (BTO) or lead zirconate titanate, gallium phosphate or a lead-magnesium niobate, or zinc oxide (ZnO) or aluminium nitride as a thin-layer deposit or polarized polyvinyl fluoride.

The respective material should be as transparent as possible in the infrared frequency range, advantageously in the mid-infrared frequency range.

The above-mentioned piezoelectric materials can be provided as a thin layer on a measuring body and form the measuring surface. The layer thickness should then be less than 0.5 mm, in particular less than 300 microns, and/or have a recess or slot, such as a bored hole or a channel for the excitation beam. The remaining part of the measuring body may then not be piezoelectric and transparent to the excitation beam and/or have a recess for the excitation beam. This remaining part of the measuring body can act as a heat sink for the coating with a piezoelectric material, which means it can have a greater specific thermal capacity and/or thermal conductivity than the piezoelectric layer.

A further implementation of the device can provide that a piezoelectric element or a piezoelectric region of the measuring body can be connected as an actuator to a voltage source and depending on a controllable input voltage, forms a blockage for an excitation beam.

In this way, the material of the measuring body can also be used as an optical chopper for the excitation beam by changing the dielectric constant.

A method for operating a device according to the invention can provide that a modulated excitation beam is directed, in particular through the measuring body, onto the substance to be analysed and that signals from different electrode pairs of the contact device are acquired and evaluated simultaneously or sequentially, that it is firstly determined based on criteria which one or more of the pairs of electrodes delivers/deliver signals suitable for further processing, and that the signals from one or more selected electrode pairs are then used for measurement and evaluated, and that, in particular, a subsequent measurement is performed in which the signals of the selected electrode pair or pairs are acquired and evaluated.

Suitable signals can be selected, for example, based on the strength of the signals, the signal/noise ratio or the steepness with which the signals follow the modulation of the excitation beam. With the selection of the suitable electrodes, it is possible if applicable to detect and correct any misalignment of the substance to be analysed with respect to the measuring device, if e.g. the thermal wave does not reach the centre of the measuring region. In this case, differently distributed electrodes are selected for the current measurement.

During the measurement, the excitation beam is modified continuously or in steps with respect to the wave number/ wavelength/frequency, or characteristic wavelength ranges are scanned. When using an array, an excitation beam can also be emitted simultaneously or sequentially through different elements of an array at different wavelengths or in different wavelength ranges.

In one implementation of the method it can also be provided that, after an initial test measurement, depending on the signals detected a misalignment of the device relative to the substance to be analysed is determined and indicated and, in particular, the user is requested to perform a re-alignment.

This method can even be used in parallel with another detection method, for example with a reflected detection beam, to detect and signal only misalignments of a finger on which a measurement is to be performed.

Misalignments can be detected, for example, by determining the signal strengths of different pairs of electrodes in an initial measurement in the form of a profile/vector and comparing this profile/vector with corresponding values from previous measurements or specified reference values. The specific profile can also be normalized to a signal strength. If the difference relative to a reference profile exceeds certain thresholds for certain elements of the profile or with regard to asymmetry, then a misalignment can be inferred.

In a further implementation of a method, it can also be provided that with an excitation transmission device, at least one intensity-modulated electromagnetic excitation beam with at least one excitation wavelength is generated, the excitation transmission device irradiates the at least one electromagnetic excitation beam into a volume of substance which is located below the surface of the substance, a response signal is detected with a detection device, and the substance is analysed on the basis of the detected response signal, wherein using different modulation frequencies of the excitation transmission device, response signals, in particular temporal response signal waveforms for different wavelengths of the excitation beam, are successively determined and a plurality of response signal waveforms at different modulation frequencies are correlated with one another and wherein information specific to a depth range under the surface of the substance is obtained from these.

FIGS. 1 to 17 show schematic drawings of different elements of the device and its elements, in some cases in different embodiments, also shown are FIG. 18: a cross-section of a measuring body with a first integrated lens and a finger placed on the measuring surface, FIG. 19 a cross-section of a measuring body with a second integrated lens, FIG. 20 a cross-section of a measuring body with a third integrated lens, FIG. 21 a cross-section of a measuring body with a first integrated lens and an excitation beam, FIG. 22 a cross-section of a measuring body with a second integrated lens and an excitation beam, FIG. 23 a cross-section of a measuring body with a third integrated lens and an excitation beam, and FIGS. 24, 25, 26 several arrangements with a measuring body and an excitation light source in the form of a laser light source or excitation light source, in particular a laser device, wherein the excitation light beam is guided through the measuring device to the measuring surface by means of an optical waveguide integrated into a substrate of the measuring body.

FIG. 1 shows an exemplary embodiment of a device for analysing a substance. The substance 5 is preferably located directly on a measuring body 1 or vice versa, in either case the substance and a measuring surface 2 of the measuring body 1, which in this disclosure is also referred to as an "optical medium", are in direct physical contact for a measurement operation. The measuring body 1 may be implemented as a solid body transparent to light, or at least transparent in the infrared range, in particular a crystal or glass body or plastic body, in particular a polymer body, which is transparent, in particular in the infra-red range, for example when the device is designed for measuring glucose or blood sugar content in a liquid, such as in one embodiment, for example, blood. The device can then be used to generate a glucose or blood sugar level indication.

The device comprises an excitation transmission device 3 in the form of an excitation beam source, in particular a laser device for emitting one or more electromagnetic excitation beams, preferably in the form of excitation light beams with one or more excitation wavelengths, into a volume 5a that is located in the substance 5 underneath a first region of the surface of the substance. The excitation transmission device 3 is also briefly referred to hereafter as a laser device. The laser device can be a laser that is tuneable with respect to wavelength, in particular a tuneable quantum cascade laser; it is preferable, as explained further below, to use a light source strip or a light source array with at least two single emitters in the form of lasers, in particular semiconductor lasers with fixed wavelengths, or light-emitting semiconductor diodes, each of which emits a specified individual wavelength or light within a defined narrow wavelength range, including the possibility of using light sources combined simultaneously or sequentially with suitable filters and connected in series to isolate specific wavelengths or wavelength ranges.

If a plurality of individual emitters is combined, the individual excitation light beams can be injected into a light path jointly by means of a multiplexer, for example into a fibre-optic cable or an isolated channel or other light path in the optical medium. A collimator can also be provided to align the light beams emitted by different emitters as closely as possible parallel to each other and to combine them as much as possible into a single beam, both in the case of multiple beams of light emitted simultaneously and in the case of multiple beams of light emitted sequentially.

On the path of the excitation light, an optical element for focussing the excitation light can also be provided. This can be provided, for example, between the laser device and the measuring body, or on the measuring body itself where the excitation beam enters it, or also on the measuring body in the region where the excitation beam leaves the measuring body, for example in the region of the measuring surface, on the measuring surface, flush with the measuring surface or between the measuring surface and the detection device.

For example, the optical element can be machined from the material of the measuring body as a convex lens, or it can also consist of a different material from the material of the measuring body.

In addition, a device 9 is provided for the intensity modulation of the excitation beam(s)/excitation light beam(s), which is preferably formed by a modulation device for the excitation beam source, in particular laser device, in particular for its activation, and/or at least one controlled mirror arranged in the beam path and/or a layer, controllable with regard to its transparency and arranged in the beam path.

A thermal wave emitted after absorption of the excitation beam in the region 5a of the substance enters the measuring body where it can be detected in a detection region 4 by a detection device. This is carried out by detecting a local temperature increase or temperature change that follows the absorption very rapidly in time. Also, the reversal of the temperature change (decrease in temperature) after the end of an absorption phase (when the intensity of the excitation beam decreases as part of the modulation of the excitation beam) follows the intensity curve of the absorption intensity very quickly with a certain phase offset, which depends on the depth at which the excitation beam is absorbed in the substance.

Herein, the amplitude of the response signal depends on the wavelength of the excitation beam, the absorption properties of the sample, as well as the thermal properties, in particular the thermal diffusivity and thermal conductivity of the sample and of the measuring body/optical medium 1. In addition, the coupling of the thermal signal from the sample into the measuring body also plays a role.

In the exemplary embodiment shown, the detection device 4, 6 is formed as a region 4 of the measuring body 1, which at least partially or in some sections consists of a piezoelectric material, wherein the detection device 4, 6 also has electrodes 6a, 6b, 6c and 6d, which are arranged on respectively opposite sides of detection region 4. The electrodes 6a to 6d make an electrical contact with the material of the detection region 4 and are referred to jointly hereafter as "contact device" 6. In this way, a temperature or temperature change can be detected, depending on the material selection of the piezoelectric material, by a piezo-voltage generated between the electrodes, or by an electrical resistance or a change in resistance.

In the example of FIG. 1, the two rectangular, laminar or plate-shaped, plane electrodes 6c and 6d are arranged parallel to each other along the surface normal 7 of the measuring surface 2 at different distances from the measuring surface 2. The two electrodes 6a and 6b, which are also planar and plate-shaped, are arranged spaced apart and parallel to each other in the direction of the arrow B, perpendicular to the direction of the surface normal 7 and parallel to the measuring surface 2. The coordinate system formed by arrows A, B and C, in which the arrow A is parallel to the surface normal 7 of the measuring surface 2 and arrows B and C are oriented perpendicular thereto, is also drawn in FIGS. 2 to 15 for orientation purposes, as shown in FIG. 1.

An evaluation device 16 for analysing the substance, which is designed as an electronic device, in particular a digital processing device, for example as a microcontroller or processor or as a computer, is in electrical contact with the electrodes 6a, 6b, 6c and 6d of the contact device 6 via electrical cables 17, 18, evaluates the detected response signals and generates a glucose or blood sugar level indication (BSI) in one embodiment.

The evaluation device 16 is also electrically connected to the modulation device 9, so that the information about the frequency/wavelength of the excitation beam and in particular the frequency and/or phase of the modulation, is available in the evaluation unit 16 and can be taken into account in the evaluation. In this way, for example, the phase shift of the response signals relative to the modulation function of the excitation beam can be evaluated to obtain information about the depth in the substance, i.e. also the distance from the measuring surface 2 or the detection region 4, at which the response signal was generated. This allows information to be obtained about a depth profiling of the distribution of a detected substance, such as glucose, in the substance 5.

The information about the modulation of the excitation beam can be sent from the modulation device 9 to the evaluation device 16, but it may also be provided that the control device 16 directly controls the modulation. The evaluation device 16 can also have a lock-in amplifier for the evaluation, which evaluates the signals specifically at the modulation frequency.

The arrangement of electrode pairs 6a/6b, 6c/6d shown is only an example. A single pair of electrodes may also be sufficient, but it is important that at least a portion of the detection region 4 must be located between the two electrodes. In addition, for optimum function, the substance to be analysed, such as a finger of a test subject, must be placed at the designated point on the measuring surface 2. Any lateral displacement of the finger/substance may cause the heat pulse not to exert its effect accurately between the electrodes and the measurement readings to be suboptimal or incorrect.

The electrodes 6a, 6b, 6c, 6d can be inserted into or attached to the measuring body 1 by an additive method (3D-printing), by moulding, evaporation, doping, targeted alteration of the raw material of the measuring body (e.g. conversion of hydrocarbons into electrically conducting carbon by means of particle radiation or gamma radiation or laser radiation), gluing or inserting into previously introduced recesses or slots.

The operation of the device in accordance with FIG. 1 and, in this context, a method for analysing a substance 5, will be described by example in more detail for the case in which the substance 5 to be analysed is human or animal tissue and where a glucose or blood sugar level indication is to be determined as part of the analysis of the substance.

One or more excitation beams 8, preferably infrared beams, are generated sequentially or simultaneously with the laser light source 3. The wavelength of the infrared beam or beams is preferably in a range between 3 µm to 20 µm, particularly preferably in a range from 8 µm to 11 µm.

The excitation beams 8 are intensity- or amplitude-modulated by the intensity modulation device 9. In one embodiment, the intensity modulation device 9 generates short light pulses, preferably with a pulse frequency between 1 kHz and 1 MHz, or pulse packets (double or multiple modulation), preferably with an envelope frequency of between 1 kHz and 10 kHz.

The modulated excitation beams 8 are coupled into the optical medium/measuring body 1, in particular directly into the material of the measuring body, and, after passing through the measuring surface 2, they enter the volume 5a within the tissue 5.

It is possible for the function of the invention, but not necessary, that the excitation because passes through the measuring body 1 or enters the material of which the measuring body is made, provided it is ensured that the excitation beam 8 enters the substance 5 to be analysed on the underside of the measuring surface 2. This is illustrated by the fact that a recess/slot 13 is represented in FIG. 1 as a potential recess, which forms a narrow channel, for example a bored hole, which merges into the measuring surface 2 on the underside of the measuring body 1 and through which the excitation beam 8 can reach the underside of the measuring surface 2 and enter the substance 5. It is in this broad sense that the above-mentioned feature, whereby the initial beam "passes through the measuring surface 2", is to be understood. Normally, a structure without such a recess 13 can be provided, provided that the excitation beam 8 can pass readily through the material of the measuring body 1. Such a recess 13 can also only partially penetrate the measuring body. Instead of a recess 13, an integrated optical waveguide can be provided in the same region, into which the excitation beam can be injected. This can end in or on the measuring surface or a sensor layer. The optical waveguide can be integrated into a substrate of the measuring body using standard manufacturing methods. For example, if the measuring body consists wholly or partly of silicon, an optical waveguide cable can be integrated as a silicon on insulator (SOI) optical waveguide. Such an optical waveguide can have a straight or curved profile. This allows the position of the excitation beam source, in particular a laser device that generates the excitation beam, to be freely positioned relative to the measuring body.

The wavelength of the excitation beams 8—with a view to the example of a blood sugar measurement described here—is preferably chosen in such a way that the excitation beams 8 are significantly absorbed by glucose or blood sugar. The following glucose-relevant infrared wavelengths (vacuum wavelengths) are particularly suitable for measuring glucose or blood sugar and can be set individually or in groups simultaneously or in succession as fixed wavelengths for measuring the response signals: 8.1 µm, 8.3 µm, 8.5 µm, 8.8 µm, 9.2 µm, 9.4 µm and 937 µm. In addition, glucose-tolerant wavelengths that are not absorbed by glucose can be used to identify other substances present and exclude their influence on the measurement.

For a measurement, a spectral region can be continuously scanned by scanning the excitation source, in particular a laser device 3, or the spectrum can be covered discontinuously at support points by suitable specific fixed wavelengths.

If substances other than glucose are to be detected, the corresponding wavelengths are to be selected for the excitation beams, which are characteristic of absorption wavelengths for these substances.

The absorption of the excitation beams 8 in the tissue 5 causes a local temperature increase in the region of volume 5a, which triggers a heat transfer and hence associated pressure waves and thermal pulses towards the surface of the tissue 5 and the measuring surface 2 in contact therewith. Due to the temperature and pressure fluctuations that occur at the measuring surface 2 and adjacent to this in the measuring body 1, the density, refractive index or the deformation, microstructure and the reflection behaviour in the detection region 4 near to the measuring surface 2 are modulated and, as a result, in the case of a piezo-material an electrical resistance is influenced or a piezo-voltage is generated or changed/modulated as a response signal.

The magnitude/amplitude of the intensity modulation of the measured values/response signal depends on the wavelength of the excitation beams (due to the necessary absorption in the tissue) and on the pulse frequency/modulation frequency of the excitation beams (due to the heat transfer and the pressure waves from the interior of the tissue towards the measuring surface 2) and on the thermal properties of the sample and the measuring body 1.

The measurement can be performed for a plurality of different modulation frequencies and the measurement results, for example in the form of spectra, can be correlated with one another. The individual spectra represent the response signal, for example a piezo-voltage or the amplitude of a variable piezo-voltage as a function of the wavelength of the excitation beam. Different spectra can be correlated in such a way that measured values from the surface of the sample (of the substance 5) can be cancelled out/eliminated or that specific information can be obtained from a specific depth range.

Each of the spectra at a given modulation frequency arises from the superposition of response signals from the substance 5 to be analysed from different depths, since the excitation beam 8 is partially absorbed in different depth layers as it passes into the sample.

The response signal thus represents a mixture of signals from different depths.

The mixture ratio of the signals from different depths depends on the frequency of the modulation of the excitation beam 8.

By correlating different spectra at different modulation frequencies, for example, calculating differences between spectra at higher modulation frequencies and spectra at lower modulation frequencies or dividing the spectra at higher modulation frequencies by spectra at lower modulation frequencies, in each case with different weighting of the individual spectra, effects of upper layers of the substance can be eliminated or at least reduced.

On the basis of comparisons with calibration or comparison measurements carried out previously, or with reference data sets, which in one embodiment are stored in the form of comparison tables or comparison curves in a memory of the evaluation device 16, the device can provide information about the current concentration of glucose or blood sugar within the tissue or within the volume 5a and generate a corresponding glucose or blood sugar level indication. For example, the comparison tables or comparison curves may have been created based on glucose or blood sugar values obtained from blood samples analysed outside the patient's body.

The excitation beam source, which in the exemplary embodiment shown is formed by a laser device 3 for emitting the excitation light beam or beams 8, can be implemented as an array. The array has at least 5, advantageously at least 10, more advantageously at least 15 or at least 50 or 100 individually controllable emitters 100a for monochromatic light of different, fixed wavelengths in the absorption spectrum of a substance to be analysed. The individual emitters can be laser emitters, but they can also be other types of emitters, such as suitable light-emitting diodes or other semiconductor components, which selectively emit radiation in a specific wavelength range.

The array preferably produces beams of monochrome light at one or more, particularly preferably at all of the following wavelengths (vacuum wavelengths): 8.1 µm, 8.3 µm, 8.5 µm, 8.8 µm, 9.2 µm, 9.4 µm and 9.7 µm and, if desired, additionally glucose-tolerant wavelengths.

It may be provided that the excitation transmission device/excitation light source 3 is permanently mechanically connected to the optical medium/measuring body 1 either directly or by means of an adjustment device. The adjustment device preferably allows an adjustment of the distance of the excitation light source 3 from the measuring body 1 or an adjustment in the longitudinal direction of the beam and/or an adjustment in the plane perpendicular thereto.

It may also be provided that the excitation transmission device 3 and the measuring body 1 with the detection device 4, 6 are attached directly to each other or to a common carrier (not shown). The carrier may be formed by a plastic part, a printed circuit board, or a metal sheet mounted in a housing.

The carrier can also be formed by the housing itself or a part of the housing.

It may also be provided that the device for analysing a substance, with a housing (not shown) in which it is arranged, can be attached to the body, for example to the torso of a person, wherein the excitation transmission device 3 for emitting one or more excitation light beams 8 and the detection device 4, 6 for detecting the time-dependent response signal are arranged and configured in such a manner that the side suitable for the measurement and the measuring surface 2 of the device are located on the side of the device opposite the body/torso, so that the substance to be analysed can be measured on the side of the housing facing away from the body/torso, for example by the patient placing a finger on the measuring surface 2. For this purpose, for example, the housing is attached to a person's body by means of a strap that forms part of the body, in an embodiment in the form of a wristband, to a wrist. On the opposite side to the wrist, the housing then has a window that is permeable for the excitation light beam 8, or the measuring body 1, with its outward-facing measuring surface 2, is fitted directly into the side of the housing facing outwards away from the body and forms some sections of the surface of the housing itself, for example, together with the measuring surface 2.

In this design, a finger pad can then be placed on the measuring body 1 and monitored.

The measuring body 1 can be mounted inside the housing, in the same way as the carrier, or directly on the housing. The measuring body 1 can also be connected directly to the carrier, wherein an adjustment device should be provided for the positioning of the carrier relative to the optical medium/measuring body 1.

It is also possible to mount the excitation light source 3 directly on the measuring body.

Through the optical window in the housing and/or through the measuring body 1, other parameters of the substance surface or the applied finger pad can also be monitored, such as a fingerprint in one embodiment. For this purpose, an optical detector in the form of a camera can also be attached to the carrier, for example, which digitally acquires an image of the surface of the substance 5 through the measuring body or past it next to the measuring body. This image as well as the measurement information from the detection device 4, 6 is processed within a processing device wherein the processing device can be directly connected to the detection device 4, 6 and also to the excitation transmission device 3. The processing device can also perform control tasks for the measurement. It can also be at least partially separated and remote from the other parts of the device and communicate with them via a radio link.

The image data from the camera can thus be further processed inside the housing or also via a radio connection outside the housing and compared with a personal identification database in order to retrieve calibration data of the identified person and use this data as a basis for the measurement.

Such calibration data can also be stored for retrieval remotely in a database, in one embodiment a cloud. The measurement data of the detection device can also be further processed both inside and outside the housing.

If data are processed outside the housing, the result data should preferably be transmitted by radio back to the device inside the housing in order to be displayed there.

In any case, a display (not shown) can be provided on the housing, which can advantageously be read off through the optical window, in one embodiment also partly through the measuring body or on the measuring body 1. The display can also project an indicator light onto a display surface through the optical window and, for this purpose, comprise a projection device. In one embodiment the display allows a measurement or analysis result, in particular a glucose concentration, to be displayed. The output can be implemented in one embodiment using a character or colour code. In one embodiment, a suggestion for an insulin dose depending on other patient parameters (e.g. insulin correction factor), or an automatic signal transmission to a dosing device in the form of an insulin pump, can be output via the display or a signal device that is parallel to this.

Alternatively, a recommendation can be made for the consumption of certain foods in a particular quantity. This can be linked, for example, to a proposal for preparation, which can be retrieved from a database and, in particular, transmitted in electronic form. This preparation instruction can also be sent to an automatic food preparation device.

The connection of the device to and from an external data processing device can be implemented using all common standards, such as optical fibres, cables, radio (e.g. Bluetooth, WiFi), or even ultrasound or infrared signals.

Figure 2:
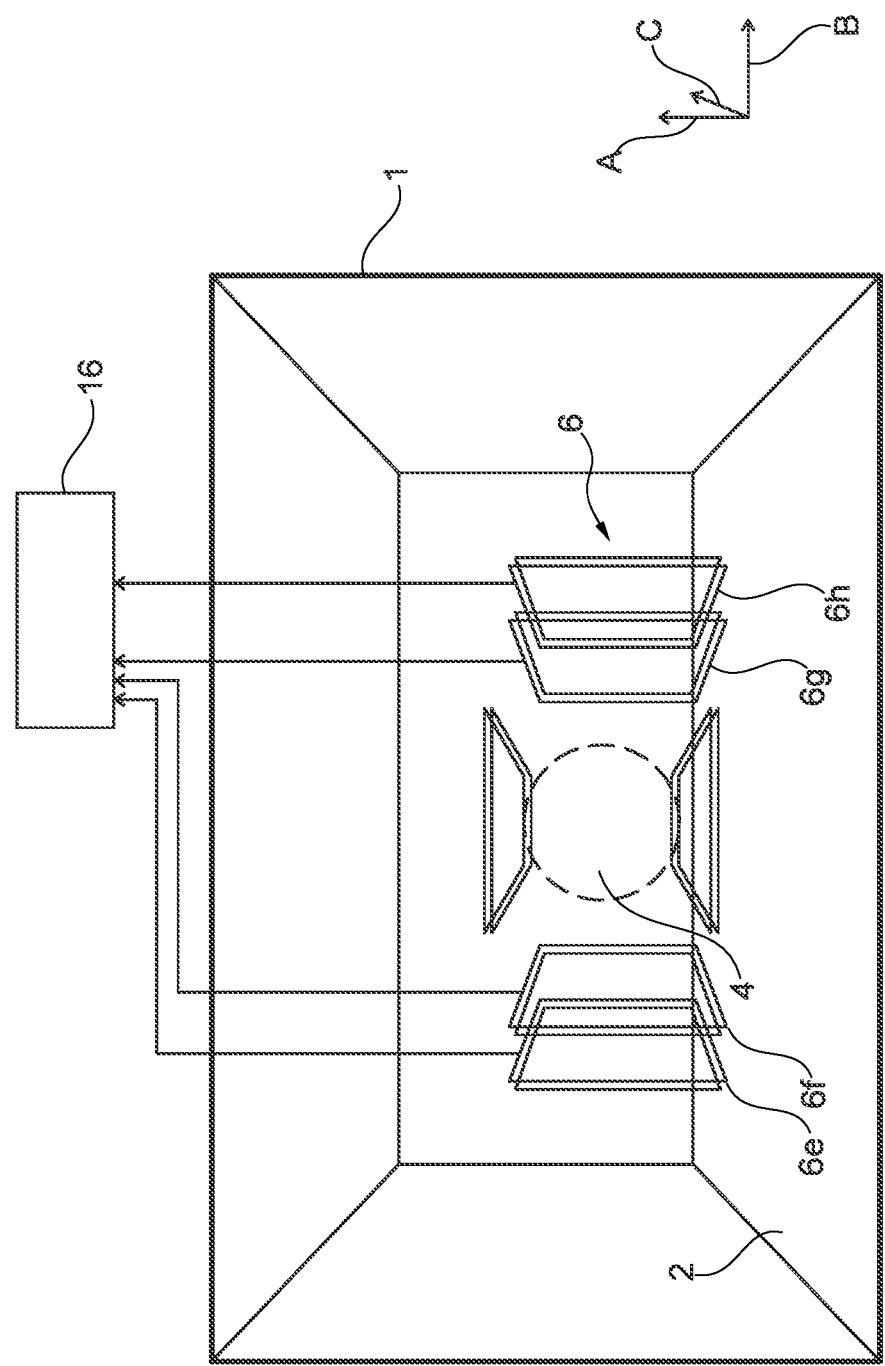
FIGS. 2 to 16 show, among other things, particular designs of the contact device 6 with electrodes distributed in a variety of ways.

FIG. 2 shows, again schematically, a measuring body 1 with a measuring surface 2 and a detection region 4 and a contact device 6. FIG. 2 also shows that the contact device 6 can also have a plurality of electrodes on each side of the detection region 4. In the example shown, the electrodes 6e, 6f are shown on a first side of the detection region 4, and the electrodes 6g, 6h are shown on the opposite side of the detection region 4. In the example shown, the individual electrodes are designed in a rectangular plate-like manner. For a measurement, the device 16 can evaluate a piezosignal (in the form of a piezoelectric voltage or a modified resistance) between two electrodes 6e, 6f, 6g, 6h and the results can be compared. A pair of electrodes can then be selected for the further evaluation of the measurement or for a subsequent measurement. The selection can take into account which pair of electrodes provides the largest signals or the signals least susceptible to interference. A pair of adjacent electrodes can preferably be selected for the measurement, for example the electrodes 6f and 6g or else the electrodes 6e and 6f or 6g and 6h. However, it is also possible to use the electrode pair 6e, 6h for a measurement and evaluate the signals present between these electrodes. In doing so, it should be noted that the electrodes that are not currently being used for a measurement can provide dielectric shielding to other electrodes. For example, the unused electrodes can be left at a floating potential or in certain cases, connected to ground potential.

Figure 3:
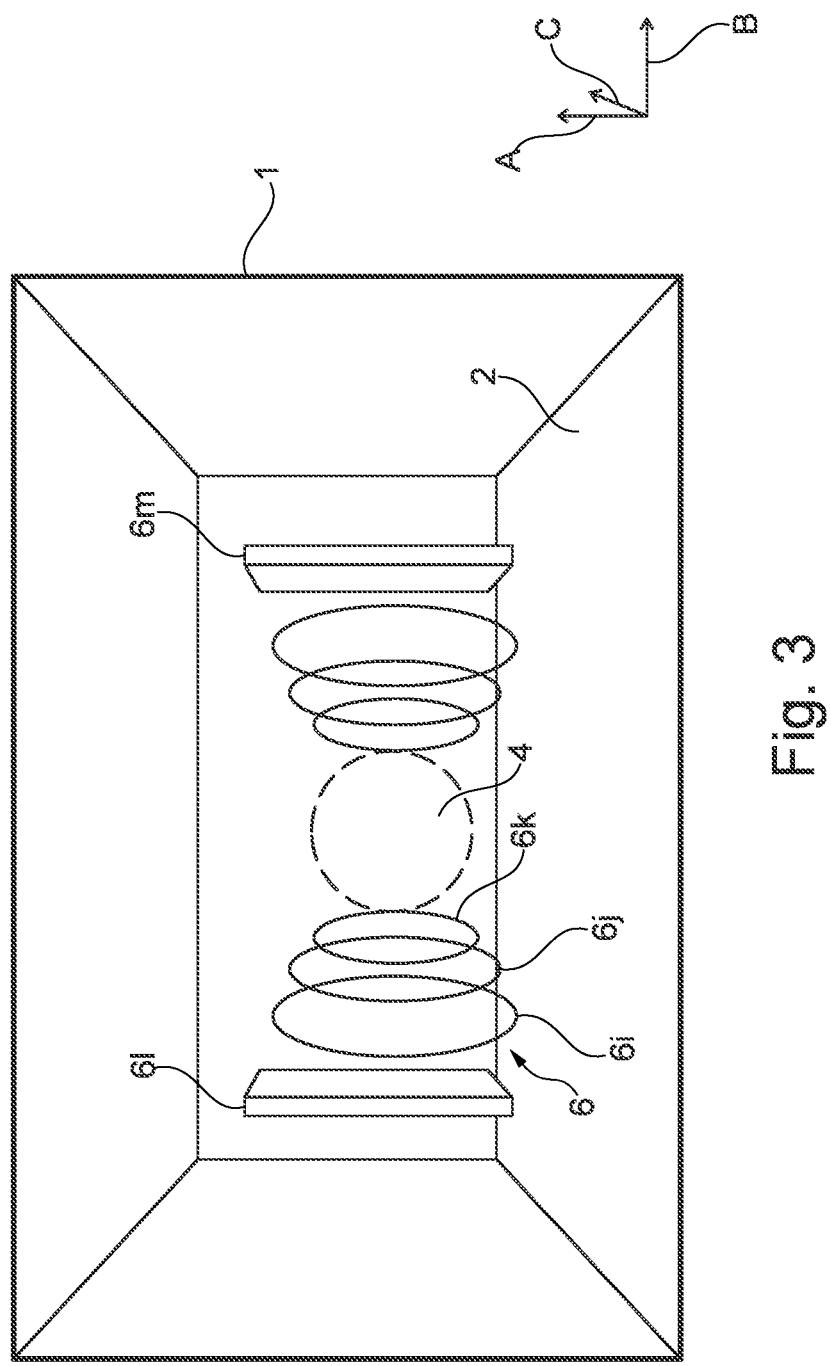

FIG. 3 shows an arrangement of a contact device 6, which has three annular electrodes 6i, 6j, 6k on each side of the detection region 4. These electrodes can also be used in pairs for the measurement. In the case shown, the diameter of the annular electrodes increases outwards from the detection region 4, so that the electrode 6i has a larger diameter than electrode 6j and this has a larger diameter than electrode 6k.

In addition, a pair of flat, plate-shaped electrodes 6l, 6m, for example, can be provided on the outside behind the electrodes 6i, 6j, 6k.

The annular design of the electrodes, together with the size that increases outwards, can result in the outer electrodes being less shielded by the internal electrodes and different electrode pairs being able to be used independently of each other.

Figure 4:
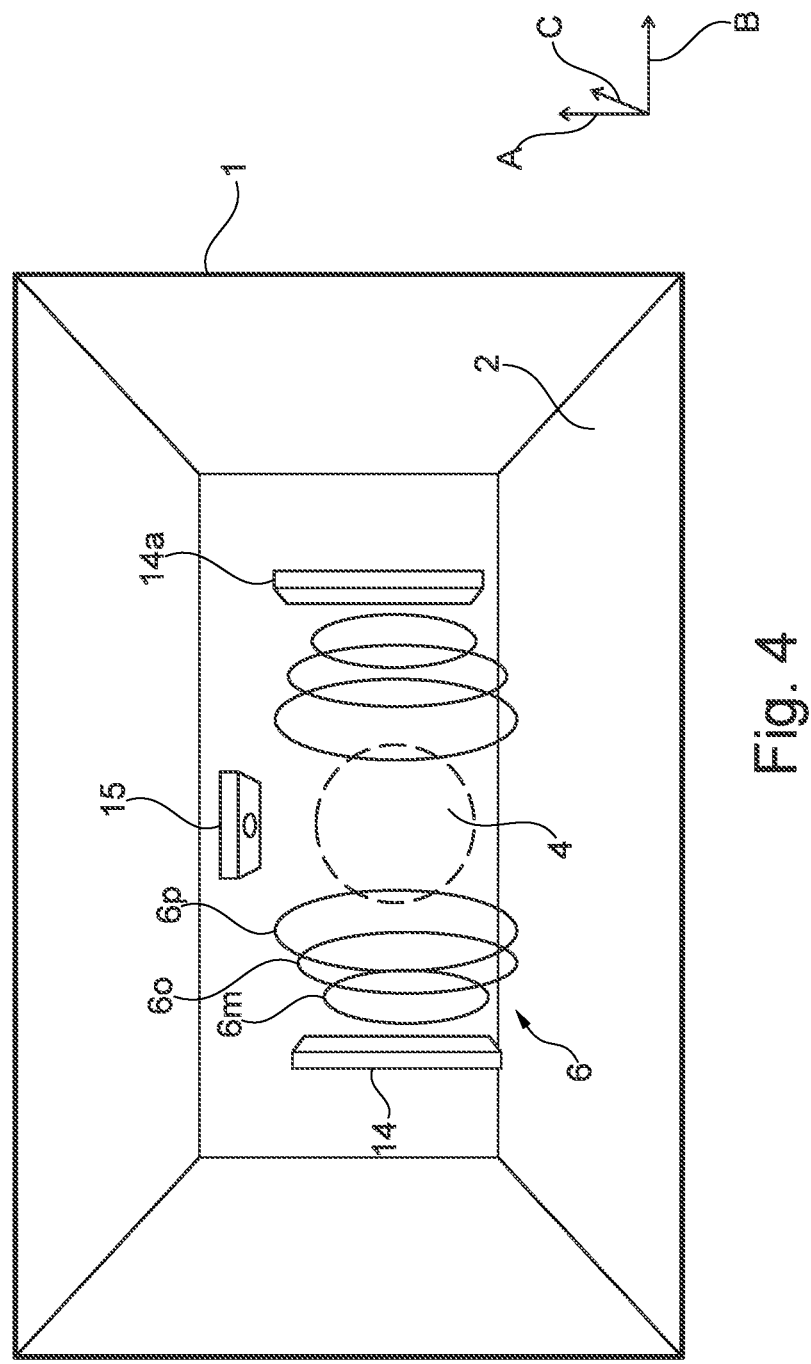

FIG. 4 shows an arrangement with a contact device 6 with three annular electrodes 6n, 6o, 6p behind each other on each side of the detection region in a horizontal direction—i.e. direction B—parallel to the measuring surface 2, wherein the diameter of the annular electrodes decreases with increasing distance from the detection region 4.

On each side of the detection region, laterally outside the electrodes, a heat sink 14, 14a is shown, which can be incorporated into the measuring body or attached to the outside thereof. For example, these heat sinks may consist of a metal or another material, the thermal capacity and/or thermal conductivity of which is greater than that of the material(s) making up the measuring body 1.

A single body, such as an annular body, may also be provided as a heat sink, which surrounds detection region 4 or the entire measuring body 1. A heat sink can also be implemented by a Peltier element. The heat sink ensures that the temperature increase caused by the arrival of a thermal wave/heat pulse in the detection region can be compensated as quickly as possible by cooling, so that the material of the measuring body 1 in the detection region 4 can react as quickly as possible to a subsequent heat pulse.

The heat pulses follow one another with the modulation frequency of the excitation beam. Above the detection region, a plate-shaped thermal barrier 15 is provided, which has an opening for the passage of an excitation beam 8. This ensures that if the thermal conductivity of the material of the measuring body 1 is too high, the heat pulse is not dissipated too quickly when it arrives in the detection region, so that a temperature increase can briefly build up in the detection region 4 before the heat is dissipated, e.g. via heat sinks.

One or more heat sinks and/or one or more thermal barriers may be integrated into or mounted on the outside of a measuring body to direct the heat transfer appropriately. This can be particularly practical for flat measuring bodies or for measuring bodies that have a thin coating of a piezo-material and are otherwise composed of a material that does not have a piezo-effect.

Figure 5:
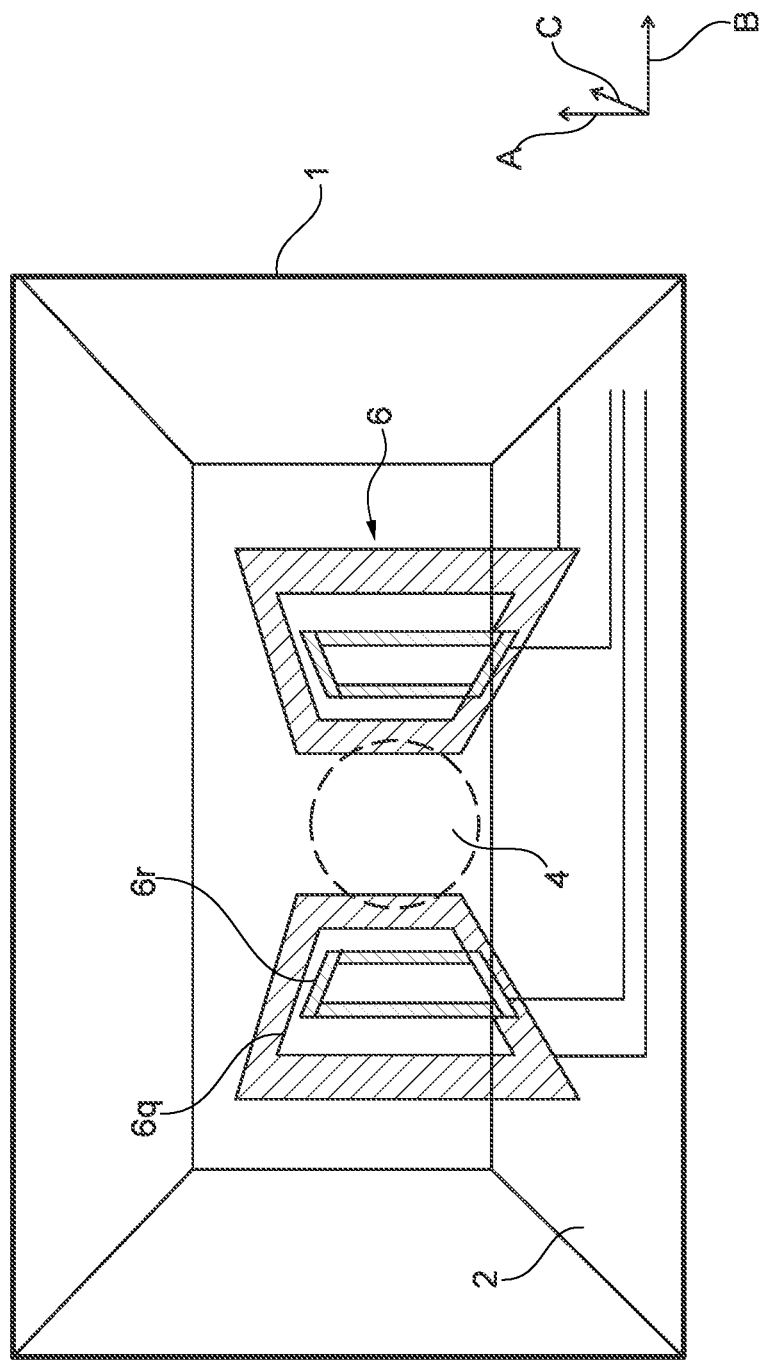

FIG. 5 shows a contact device 6 with two frame-shaped electrodes 6q, 6r on each side of detection region 4, wherein the frame-shaped electrodes are implemented as rectangular frames and can be arranged at the same distance from detection region 4 or at different distances from detection region 4. The electrodes 6q, 6r can thus be arranged, for example, coplanar and concentric to each other on each side of the detection region 4, or staggered with respect to the distance from the detection region 4.

Figure 6:
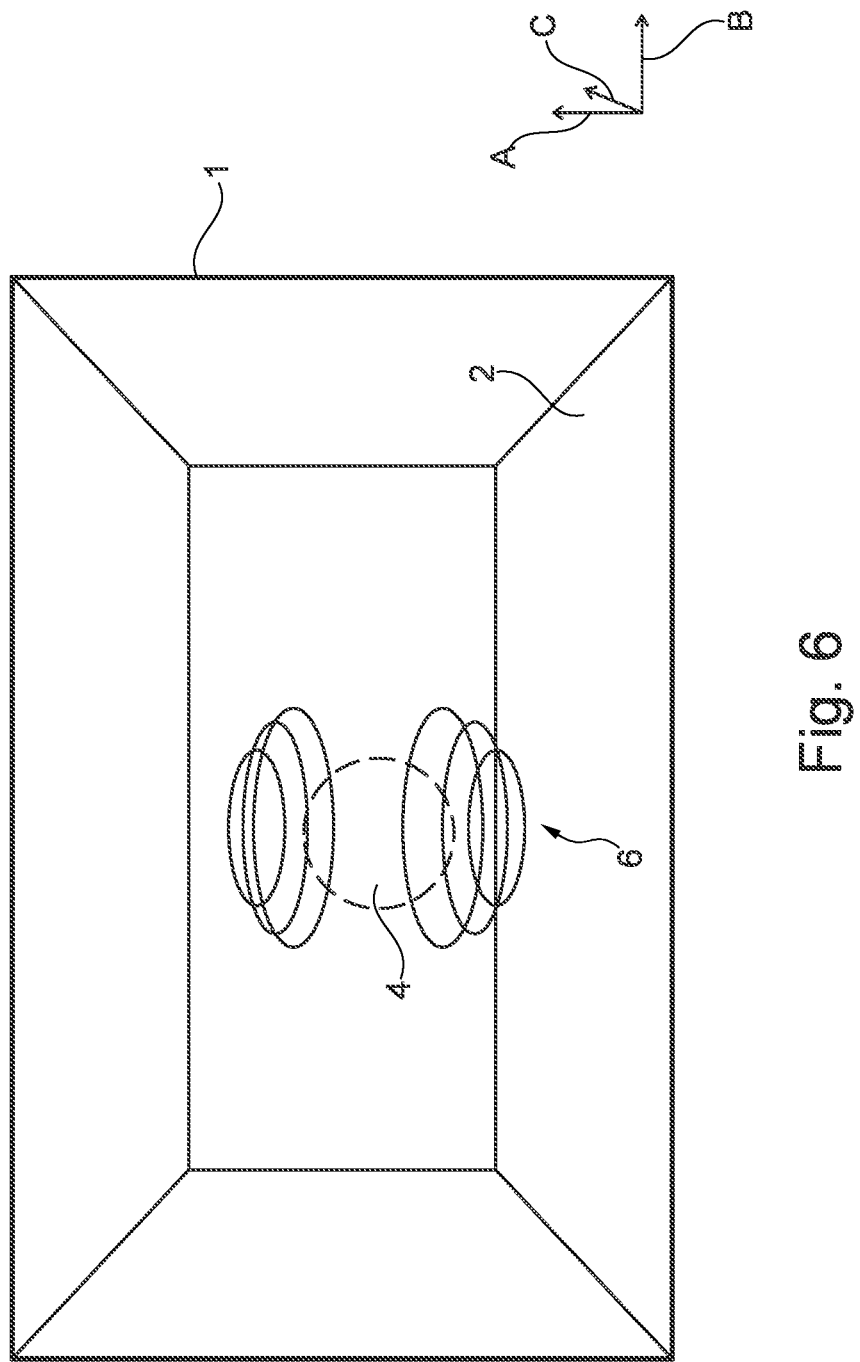

FIG. 6 shows a contact device 6 with three annular electrodes both above and below the detection region 4, i.e. the electrodes are arranged on both sides of the detection region 4, one behind the other at different distances from the measuring surface 2 with respect to the surface normal in direction A.

Figure 7:
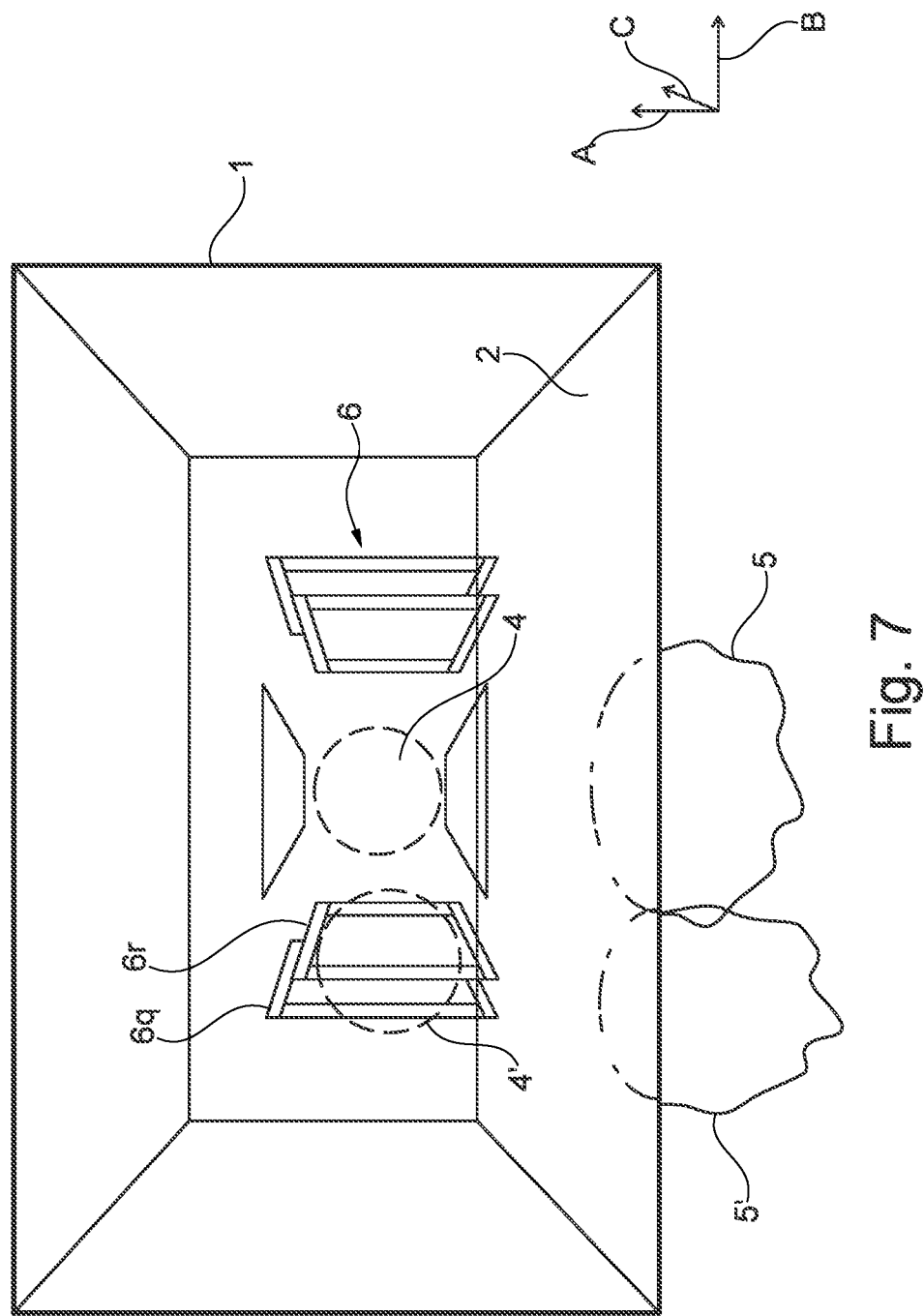

FIG. 7 shows an example of the use of electrodes of a contact device 6. On each side of the detection region 4, two frame-shaped electrodes 6q, 6r are provided at different distances from the detection region 4. Normally, if the substance to be analysed is located in the centre under the measuring surface 2, as indicated in FIG. 7 by region 5 of the substance, the selection of two electrodes on both sides of the detection region 4 can be optimal for a measurement. However, if a sample is placed on the measuring surface 2 at the wrong place, for example by subject's finger being moved laterally with respect to the optimal position, the material to be analysed will move in the direction of the position 5' shown, and an optimum detection region will lie in the region of the measuring body 1, which is designated as 4'. In this case, it may be practical to select two other electrodes, in the case shown, the electrodes 6q, 6r, for a measurement and to evaluate the electrical signals generated between them. In this case, different pairs of electrodes can also be used as a test, the corresponding signals can be evaluated and compared to each other in order to determine the exact point at which the substance 5 to be analysed is placed on the measuring surface 2 and which electrode pair produces the best results.

Figure 8:
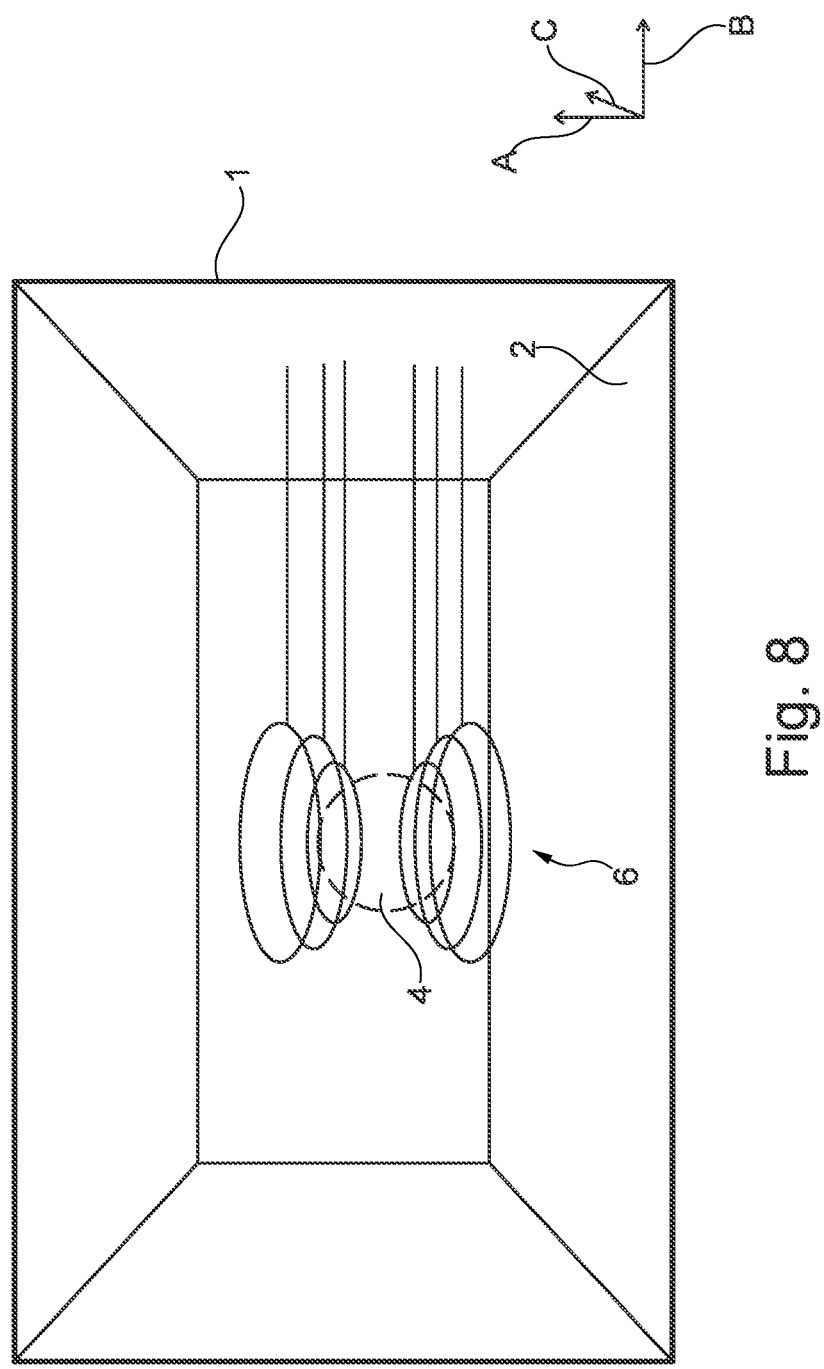

FIG. 8 shows six annular electrodes located one behind the other in the direction of the surface normal A on both sides of the detection region 4. Each side of the detection region has three annular electrodes, arranged coaxially to each other, the diameter of each electrode increasing with increasing distance from the detection region 4. Here again, different electrode pairs, which are positioned opposite each other symmetrically or asymmetrically with respect to the detection region 4, can be selected for a measurement. In this illustration, as in some of the other figures, the evaluation unit is omitted for the sake of clarity, as is an illustration of the excitation beam and the laser device.

Figure 9:
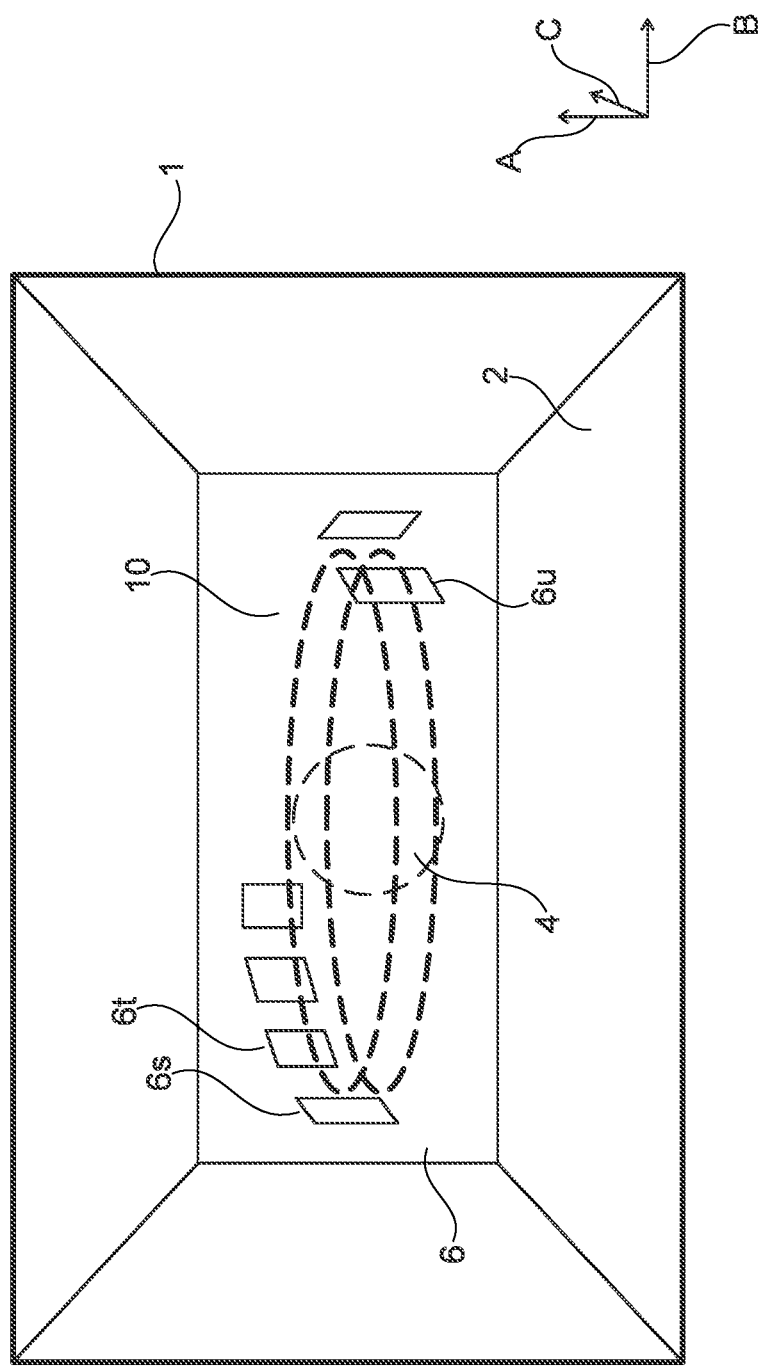

FIG. 9 shows a measuring body 1 with a detection region 4, wherein the contact device 6 has a plurality of electrodes 6s, 6t, 6u, which are distributed in an annular region m around the detection region 4. In this distribution of the electrodes 6s, 6t, 6u, it makes sense to select signals between two diametrically opposed electrodes 6s, 6u for a measurement, wherein different electrode pairs can be operated for a selection on a trial basis.

In this context, it should be noted that the detection region 4 is identified in the figures as a region of the measuring body that corresponds to the required material selection, so that it displays a piezo-effect and that at the same time is located in a region of the measuring body 1 in which a response signal from the substance 5 to be analysed arrives in the form of a heat pulse. A possible detection region 4 also depends on the electrodes 6 selected for the measurement and is usually located between the electrodes 6 selected for the measurement when the measuring body 1 in this region 4 consists of the required material or displays a piezo-effect. The detection region 4 is therefore not necessarily specified in the measuring body, but in fact is obtained as the region in which the response signals from the substance to be analysed can be detected by the selected contact electrodes 6 by means of the physical effect used when the substance 5 is suitably positioned under the measuring surface 2.

The electrodes 6s, 6t, 6u shown in FIG. 9 can be rectangular or round or oval and flat or partial cylindrical in shape, i.e. curved in one axis.

Figure 10:
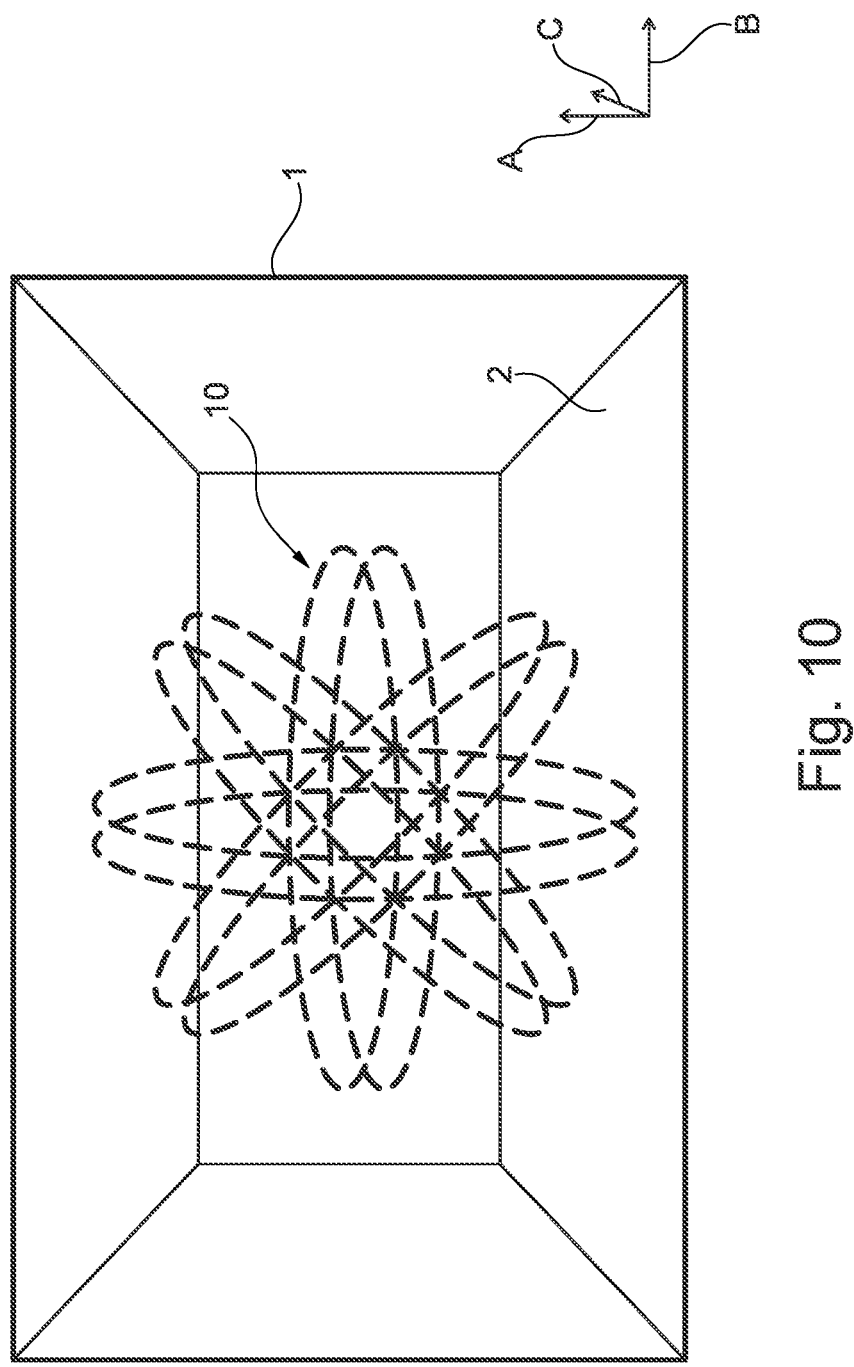

FIG. 10 shows in an example that the annular region 10, in which the electrodes are arranged around a detection region, does not need to be arranged in the form of a circular ring parallel to the measuring surface, but can be provided as a circular ring in the space of the measuring body 1 in different angular positions.

Figure 11:
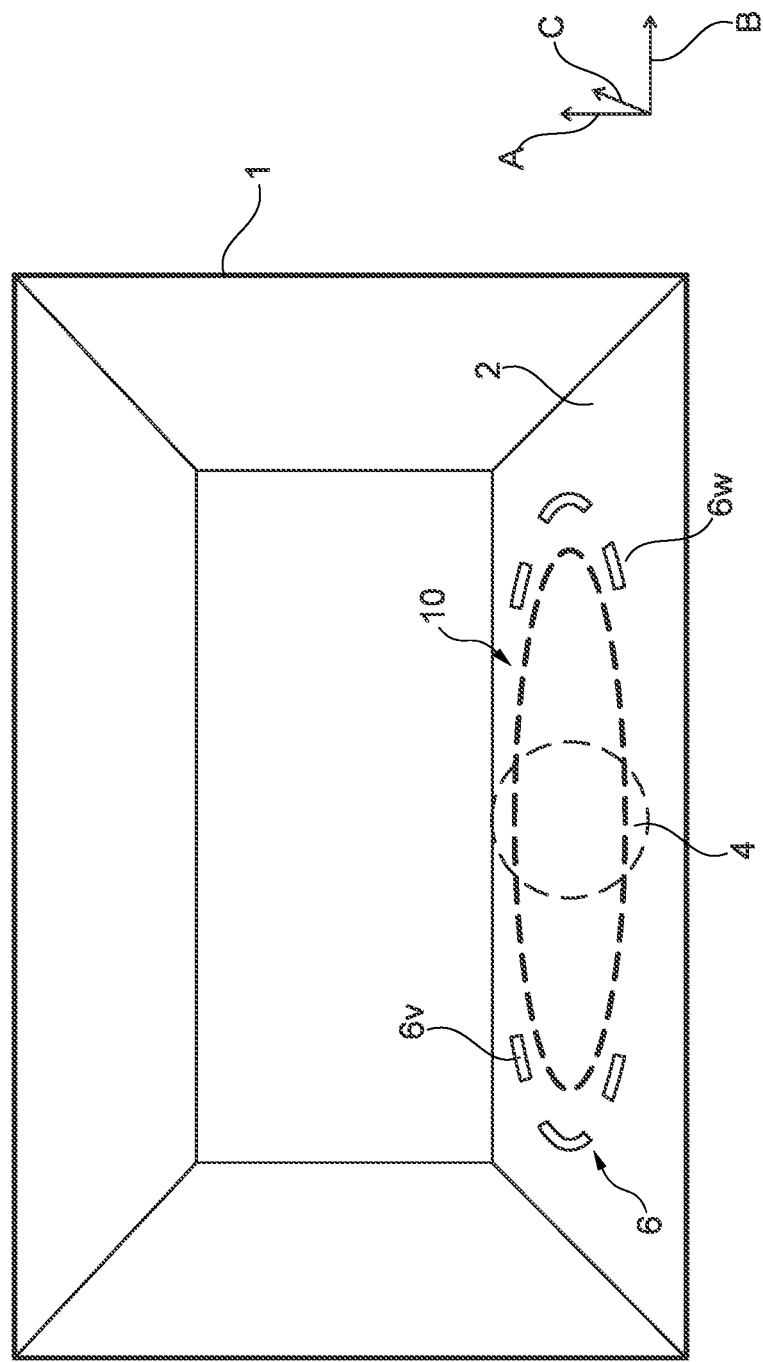

FIG. 11 shows an arrangement in which the contact device 6 is provided directly in the region of the measuring surface 2 in the measuring body 1 or on the measuring body 1. Individual electrodes 6v, 6w are arranged directly on the measuring surface 2 distributed around the detection region 4 in an annular region 10.

Figure 12:
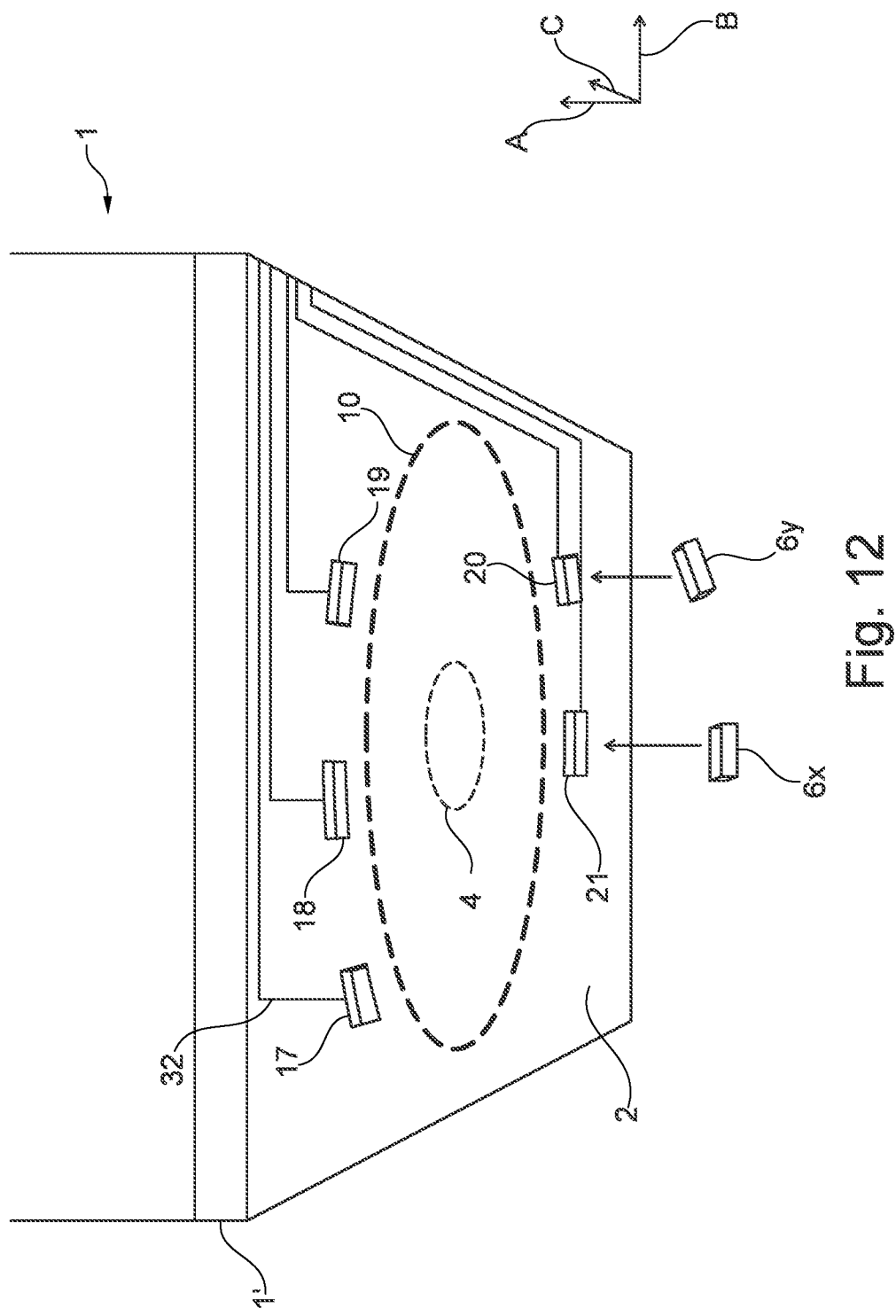

FIG. 12 shows a specific embodiment of the structure, which is indicated in FIG. 11. In FIG. 12, the measuring body 1 is shown from the underside, i.e. looking at the measuring surface 2 from the outside, wherein recesses for receiving electrodes are provided around the annular region to in a lower layer 1' of the measuring body 1. The recesses are designated by 17, 18, 19, 20, 21. Electrode bodies 6x, 6y can be placed in the recesses and can be held there in a positive-fitting or materially bonded manner. For example, the electrodes 6x, 6y can be latched in the recesses 21, 20.

The recesses 17, 18, 19, 20, 21, for example, have contacts which are connected to conductor tracks 32 on the measuring surface 2. The conductor tracks 32 are electrically connected to an evaluation device that is not shown. Upon inserting the electrodes 6x, 6y into the recesses, they are electrically connected to the conductor tracks 32 and thus to an evaluation device.

The electrodes can be selected for a measurement as already described above.

For example, it can be provided that the layer 1' of the measuring body 1 consists of a piezoelectric material, while the rest of the measuring body 1 consists of a different material, either also piezoelectrically sensitive or non-piezoelectric.

Figure 13:
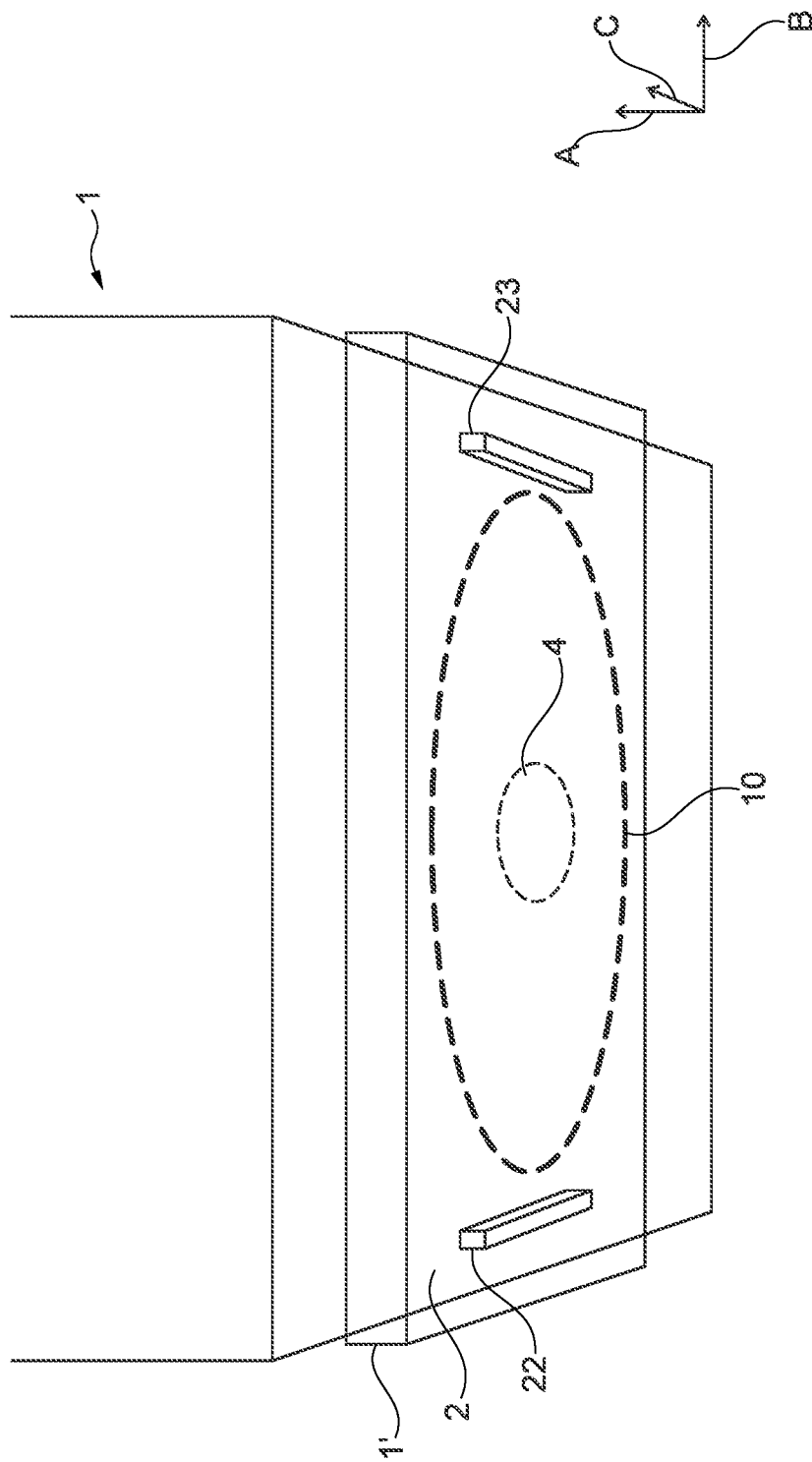

FIG. 13 shows a design variant in which the layer 1' of the measuring body 1 carries electrodes 22, 23, which are applied externally to the layer 1' (sensor layer), for example, by adhesive bonding or vapour deposition. The layer thickness of the sensor layer 1', which is made of piezoelectric material, can be between 0 and 1 mm, in particular between 0 and 500 microns, in particular less than 100 microns. The layer may be adhesively bonded to the first part/remaining section of the measuring body 1 or may be joined thereto by a different joining technique. The excitation beam can pass through this layer 1'. A channel-shaped recess for the excitation beam can be provided in the remaining section of the measuring body 1 (in the so-called first part of the measuring body 1). The material of this remaining section of the measuring body 1 can then consist of a material impermeable to infrared radiation, such as quartz or sapphire. These electrodes allow the measurement of a piezoelectric effect in the detection region 4 within the layer 1'. Other electrodes of the same type can be provided under the measuring surface 2 or in recesses in the measuring surface 2 in an annular region 10 around the detection region 4.

Figure 14:
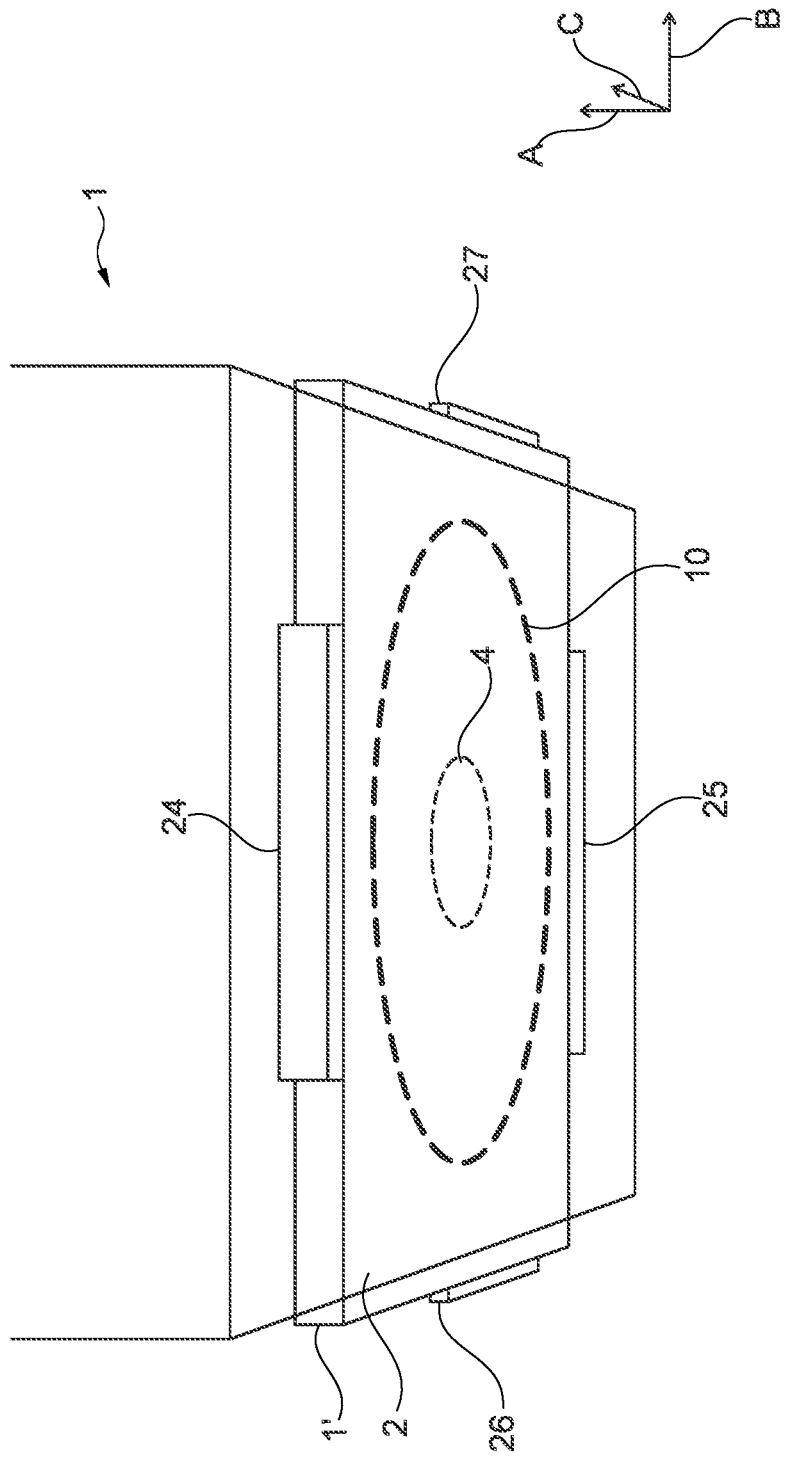

FIG. 14 shows an embodiment with a piezoelectric layer 1' of a measuring body 1, in which two electrodes 24, 25 are attached to the side of the layer 1'. These electrodes 24, 25 can also be adhesively bonded or vapour-deposited, for example, or applied in another way to the surface of the layer 1', or they can be introduced into recesses in the layer 1. The remaining side surfaces of the layer 1' can also have electrodes 26, 27, wherein all electrodes are connected to an evaluation device via optical cables or conductor tracks.

Figure 15:
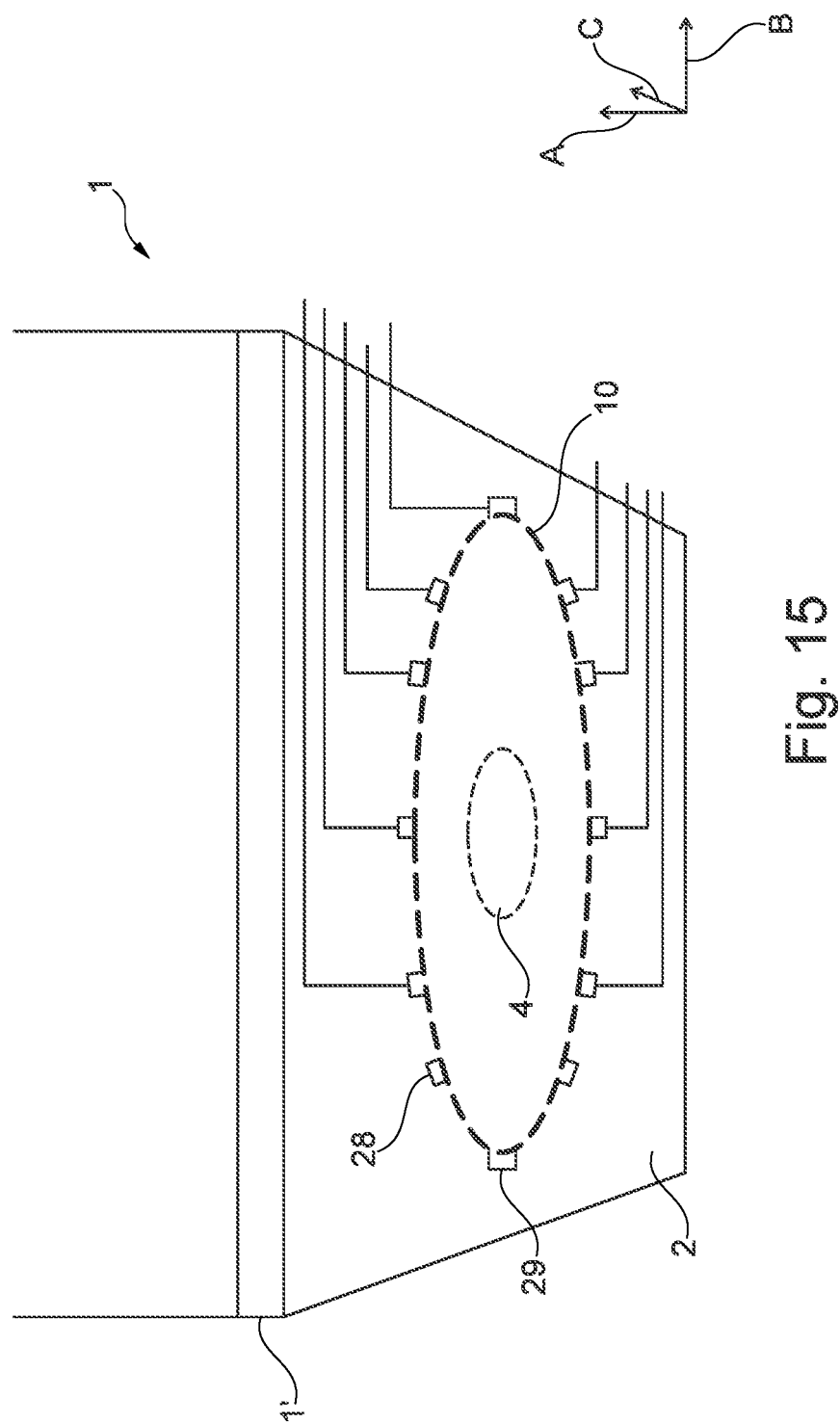

FIG. 15 shows a plurality of electrodes 28, 29, which are arranged on the underside of a piezoelectric layer of a measuring body, i.e. on the measuring surface 2, in an annular region 10 around a detection region 4. Here again, different pairs of electrodes can be used alternatively for a measurement, wherein the two electrodes of a pair are designed to be positioned facing each other on different sides of the detection region 4. These electrodes can also be adhesively bonded or vapour-deposited, for example, or applied in another way to the surface of the layer 1', or can be introduced into recesses in the layer. By experiment, different pairs of electrodes can be assembled and operated for a measurement in order to select the optimal electrode pair depending on the positioning of the substance 5 under the measuring surface 2, i.e. depending on the position of the optimal detection region 4.

Figure 1:
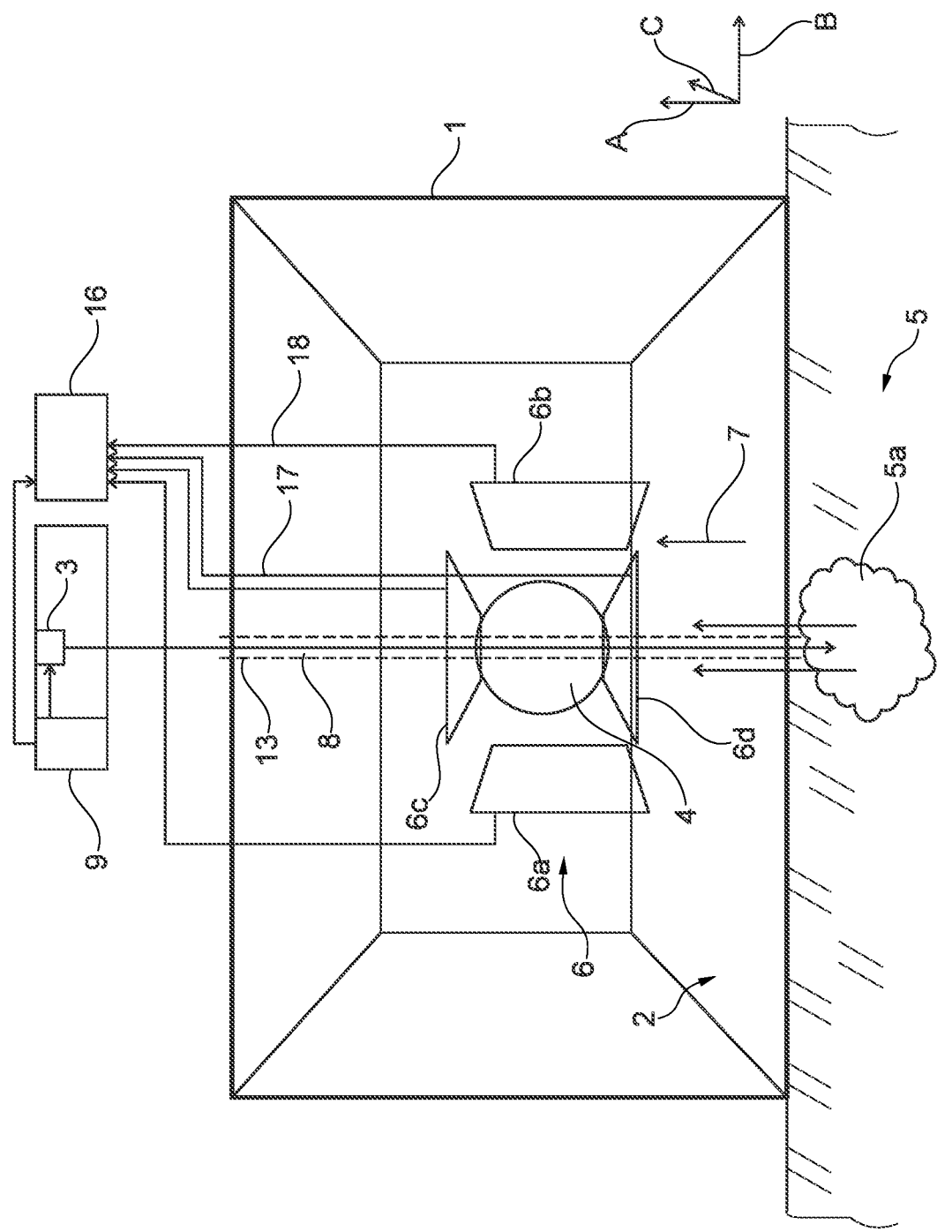
Figure 16:
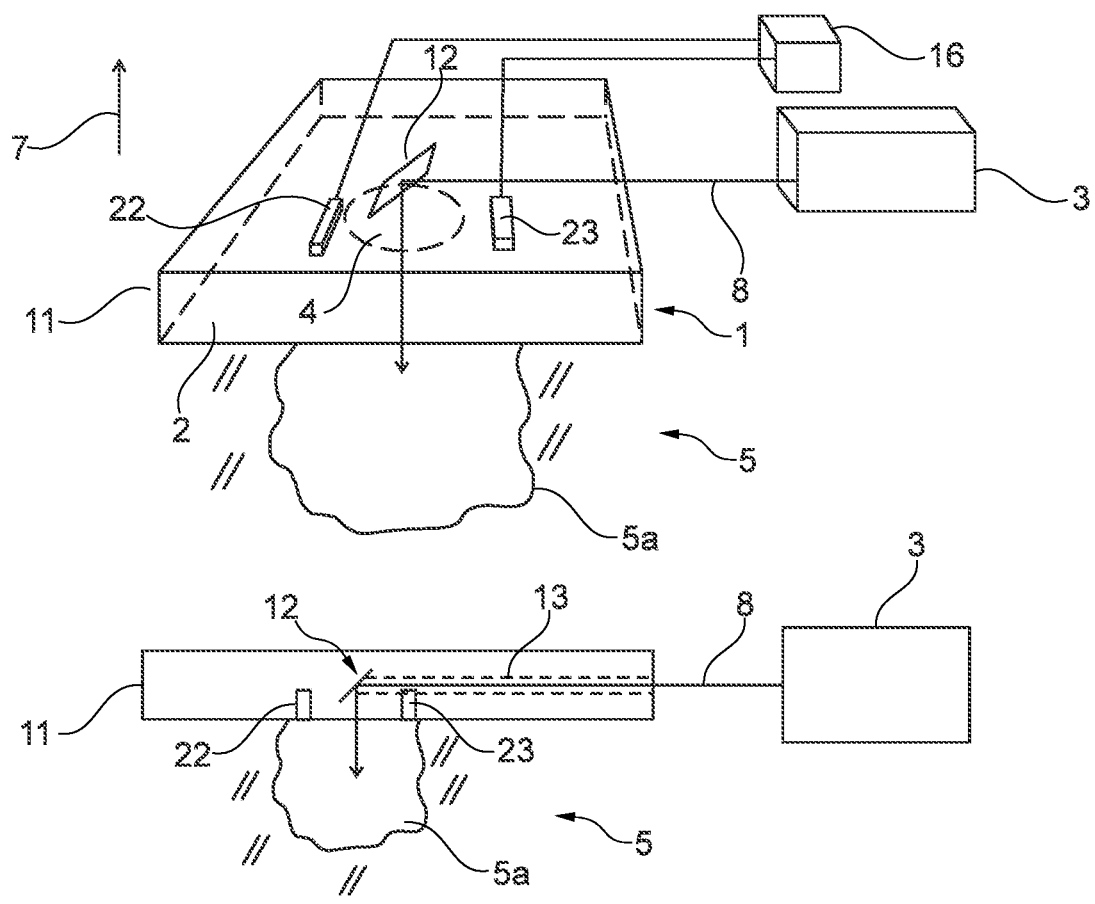

FIG. 16 shows a measuring body 11, which is designed as a flat body and can be, for example, similarly designed and equipped with electrodes as the layers 1' of the measuring body 1 shown in FIGS. 14, 15. However, in this case, the entire measuring body 1 can be formed by the flat body 11. On the underside of the flat body 11, the measuring surface 2 is provided and the extension of the flat body 11 in the direction of the surface normal 7 of the measuring surface 2 is small in comparison to the extension in the directions parallel to the measuring surface 2. In order to take up a minimum of space along the surface normal 7 for the installation of the device, it may be provided to arrange the laser device 3 to the side of the flat body over an imaginary extension of the measuring surface on one of its flat sides and to irradiate the excitation beam 8 into the measuring body/flat body 11 parallel or substantially parallel to the measuring surface 2. For the excitation beam 8, a channel-shaped recess can then be provided in the flat body, similar to that shown in FIG. 1 under reference sign 13. For example, a mirror device 12 is then provided inside the flat body, which reflects the measurement beam 8 towards the measuring surface 2 and then through the measuring surface 2 into the substance 5.

The flat body can also consist entirely of a piezoelectric material or have a piezoelectric layer in the region of the measuring surface.

Alternatively, it may also be provided that the laser device 3 is positioned slightly above the flat body 11, so that the excitation beam 8 is radiated parallel to the flat body to a mirror device 12 arranged on top of the flat body 11 and reflected there into the flat body 11 perpendicular to the measuring surface 2. In both cases, the extension of the device in the direction of the surface normal 7 is drastically reduced compared to the embodiment shown in FIG. 1. The measuring body 11 and the laser device 3 can thus be accommodated together in a flat housing, possibly together with the evaluation device 16.

Electrodes 22, 23 can be provided inside, below or at the side of the flat body 11, which are used for the measurements on the detection region 4. In this design, any of the arrangements of two or more electrodes described above can also be used.

Also, such a measuring body formed as a flat body 11 can be formed from a first part and a sensor layer, e.g. a piezoelectric layer, joined/glued to these parts, wherein the piezoelectric layer then forms the measuring surface and is equipped with electrodes. In this case also, a recess can be provided for the excitation beam in the first part of the measuring body 11, which can then optionally consist of a material impermeable or not very permeable to infrared radiation, such as quartz or sapphire.

In the lower part of FIG. 16, the arrangement shown above in a perspective view is shown in a side view in order to make clear the reflection path of the excitation beam 8.

In the event that a flat body described above is used with a laser device which is positioned at the side of it and aligned in such a way that it emits an intensity-modulated excitation beam which varies in wavelength, substantially parallel to the measuring surface in or above the flat body, wherein the excitation beam is diverted to the measuring surface, a measurement beam produced separately by a beam source, which is injected into the measuring body and reflected in the region of the measuring surface, can be used for detection, the deflection (deflection angle) of which in the measuring body in the region of the measuring surface is influenced by the response signals from the substance to be analysed. The deflection angle can be measured and used to determine the intensity of the response signals, which corresponds to the absorption intensity of the excitation beam in the substance 5 and the density/concentration of an absorbing substance/substance to be detected in the substance.

Even for such an application, the flat body may be constructed homogeneously from a material, the refractive index of which depends on the temperature, or it may have a layer in the region of the measuring surface made of a material, the refractive index of which depends on the temperature.

Figure 18:
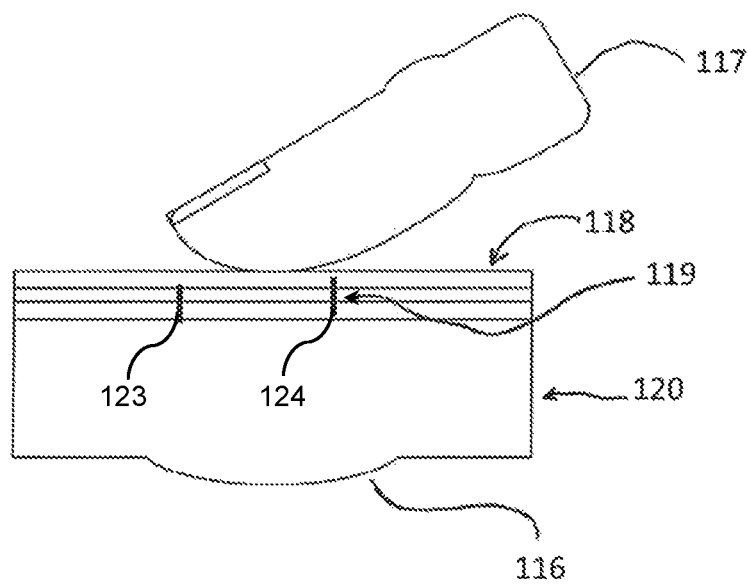

FIG. 18 shows, like FIGS. 19 to 23, a cross-sectional view of a substrate 120, into which a first electrode arrangement 119 with two schematically drawn, parallel plate electrodes 123 and 124 is embedded as part of a piezoelectric detection device. Hatching is omitted in cut portions for the sake of clarity. The measuring surface 118 is located in the upper part of the substrate 120 in each figure, which can consist entirely or partially of silicon. As an illustration, in FIG. 18 and FIG. 20 a human finger 117 is shown as an example measurement object, the substance of which is to be analysed. The finger is placed on the measuring surface 118 for analysis.

In FIGS. 18 to 23, substrates 120 are shown respectively in the region of the measuring body, the material of which is permeable for an excitation beam 121 in the infrared range, in the medium infrared range or generally in the wavelength range of the excitation beam 121. For example, this applies to a silicon substrate 120 for the mid-infrared range. In addition to the substrate 120, the measuring body can comprise other bodies and layers, such as the piezoelectric regions/the detection region and one or more covering layers for the mechanical protection of the measuring surface 118 and/or for impedance matching, which are shown schematically in FIGS. 18-23 adjoining the measuring surface 118. An excitation beam 121, provided that the substrate 120 is transparent for its wavelength ranges, can be directed through the substrate material onto the measuring surface 118 and through it into the substance to be measured (e.g. the finger 117). In such a case, it is not necessary to provide an opening in the substrate 120 for the excitation beam 121. The excitation beam 121 can be steered past or through the electrode device 119.

On the opposite side of the measuring body or the substrate 120 to the measuring surface 118, a lens 116, 116', 116" is integrated into the substrate 120, in particular formed by the material of the substrate 120 and extracted from the material of the substrate, for example by means of abrasive methods, in particular by etching or sputtering.

Figure 19:
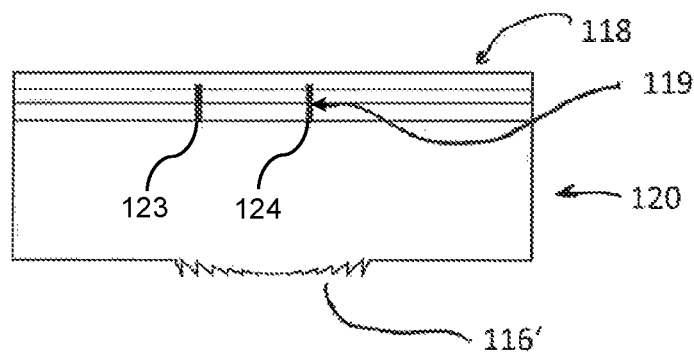
Figure 20:
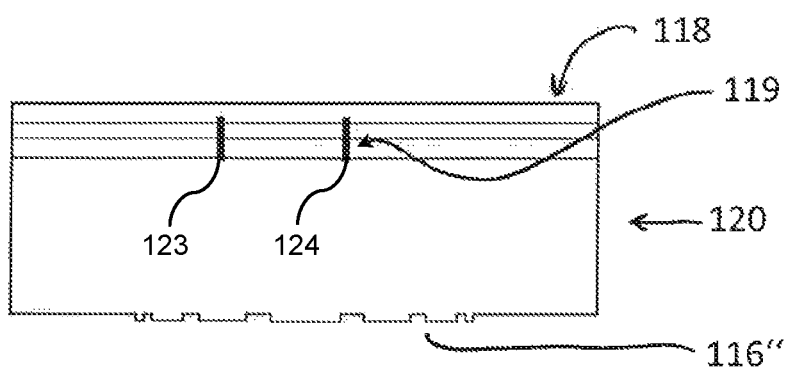
Figure 21:
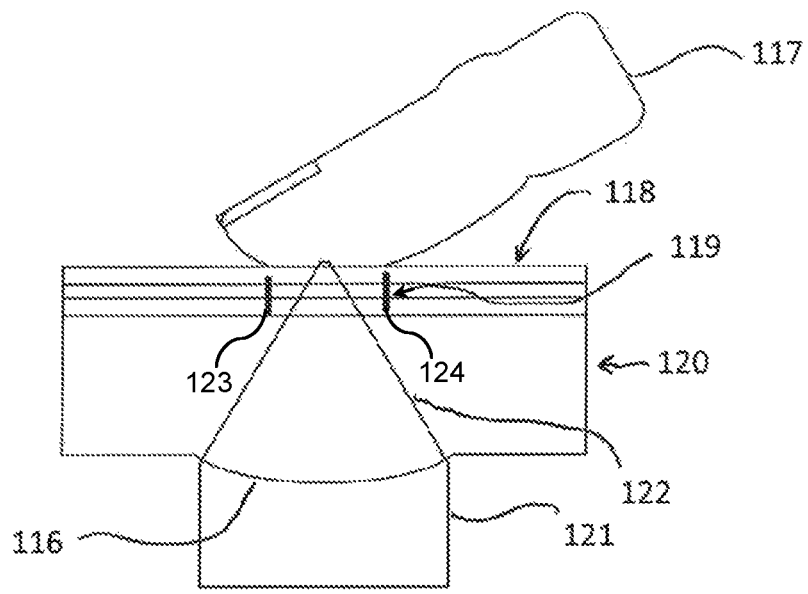
Figure 22:
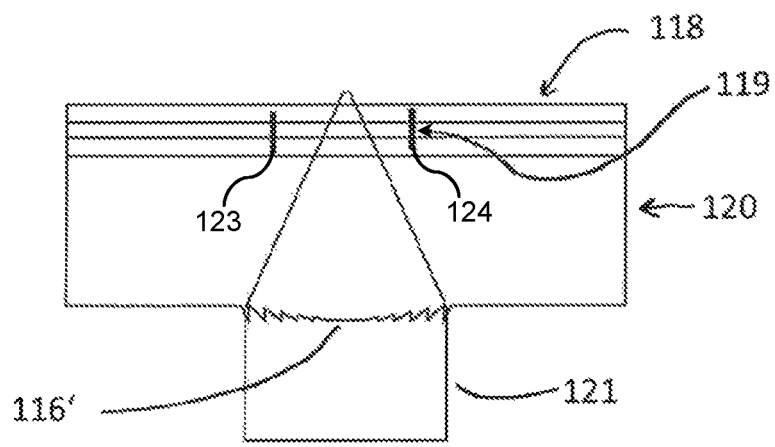
Figure 23:
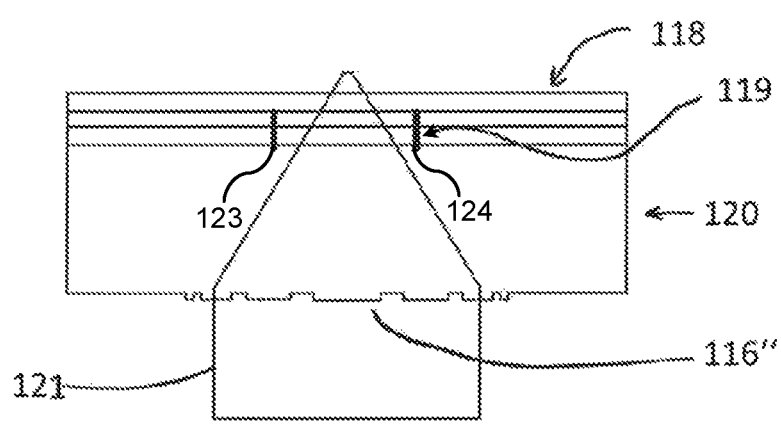

Three examples of possible lens shapes are shown in FIGS. 18 to 23, the first lens being shown in FIGS. 18 and 21, the second lens in FIGS. 19 and 22 and the third lens in FIGS. 20 and 23.

The first lens 116 corresponds to a normally refracting, refractive convex convergent lens, the second lens 116' corresponds to a (refractive) convergent lens ground to the Fresnel form (Kinoform lens), and the third lens 116" corresponds to a diffraction lens, which focusses the excitation beam 10 by diffraction at a concentric lattice structure. The optical axes of the lenses 116-116" can each be positioned vertically on the measuring surface 118, so that an excitation light source can pass straight through the substrate 120 directly. However, the optical axes can also be inclined with respect to the perpendicular to the measuring surface 118 in order to allow a potentially space-saving positioning of the excitation light source at an angle to the substrate.

FIGS. 21, 22 and 23 each show the lens shapes 116, 116', 116" on the substrate 120 with the excitation beams 121 and the focussed beams 122 focused on the substance to be analysed.

Figure 24:
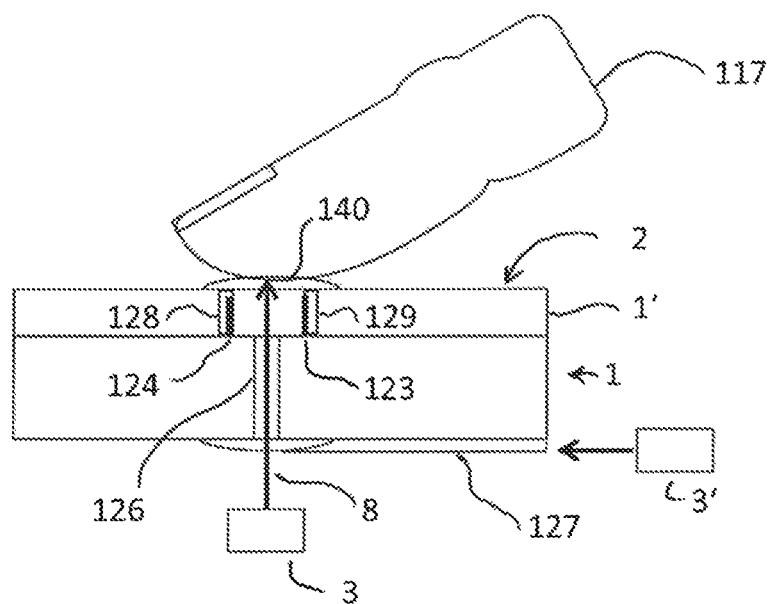

FIG. 24 shows a measuring body 1 with a sensor layer 1' in cross-section, in which an excitation beam 8 is directed out of the laser arrangement 3 into an optical waveguide 126, which passes through the measuring body 1 to the layer 1'. The optical waveguide 126 can also extend through the layer 1' as far as the measuring surface 2, but it may also be provided that either the layer 1' has a slot for the excitation beam 8 or the excitation beam 8 radiates through the material of the layer. In the region of measuring surface 2, for example directly adjoining the measuring surface 2 and/or within the layer 1', a lens 140 can be provided to focus the excitation beam 8 on a point in the substance to be examined. The optical waveguide 126 runs straight from the laser device 3 to the measuring surface 2 and passes through the detection device and/or the region between the electrodes 123, 124. To avoid an interference between the piezoelectric effect and the resulting force action of the material of the detection region on the optical waveguide, the latter may consist of a material that has no or a minimal dependence of the refractive index on external forces or pressure. An optical waveguide can also run partially or completely along the surface of the measuring body, for example, if the laser device is positioned at the side of the measuring body (see FIG. 26). In FIG. 24, the optical waveguide 127 runs from the laser device 3' first on a first part of its length at or on the surface of the measuring body, to then continue to pass through the measuring body over a second part of its length, as the optical waveguide 126. The excitation beam 8 can be reflected, for example at a mirror, in the region of the change of direction of the optical waveguide, or the optical waveguide can be bent there. Such an optical waveguide 126, 127 can be integrated into the material of the measuring body by manufacturing techniques (e.g. by SOI—silicon on insulator technology), or connected thereto as a fibre-optic waveguide by adhesive bonding, for example, or the optical waveguide can be integrated over one part of its length and implemented as a fibre-optic cable over a different part of its length.

FIG. 24 also shows that electrodes 123, 124 are usually provided in recesses or slots in the measuring body. These recesses or grooves 128, 129, which in this case are sealed with a polymer by casting, are used to separate a detection region and thus a piezoelectric body defining the detection region, which can expand and contract as a result of a thermal and/or pressure wave, thereby showing the piezoelectric, measurable effects. These can then be detected by the electrodes.

Corresponding recesses or grooves 128, 129 can be provided on all electrodes shown in this text in the various measuring bodies and may be cast with a non-piezoelectric material, such as a polymer.

The material recesses 128, 129 can be provided, for example, during the production of the measuring body 1 or introduced later by etching or sputtering, or by sawing or laser cutting.

Figure 25:
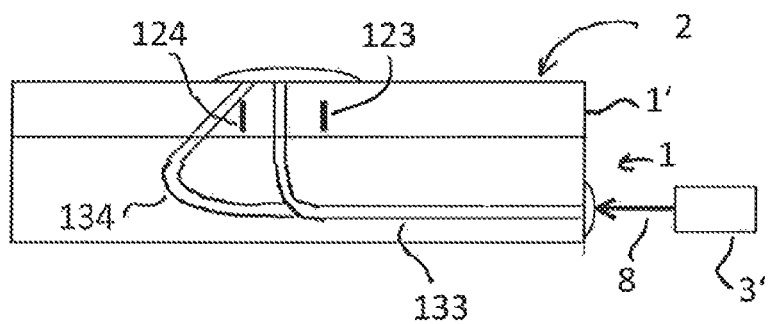

However, as can be seen from FIG. 25 in two different variants of the optical waveguide design, a curved optical waveguide 133, 134 can also be provided, which guides the excitation beam from a position on the measuring body 1, on which the laser device 3' is provided, to the measuring surface 2. The fact that the route of the optical waveguide 133, 134 can be shaped relatively freely allows a minimum distance to be maintained between the region penetrated by the excitation beam 8 and the detection region. The excitation beam 8 can also strike and pass through the measuring surface 2 at an angle between 0 degrees and 60 degrees, in particular between 0 and 45 degrees to the surface normal of the measuring surface 2.

Due to the low penetration depth into the substance to be analysed, the region of the substance in which the excitation beam 8 interacts with it lies directly below the detection device and electrodes 123, 124, despite an oblique irradiation direction. For example, the curved optical waveguides 133, 134 can be provided at least in sections as fibre-optic cables in a bored hole or similar recess of the measuring body 1, where they are glued or cast in place.

Figure 26:
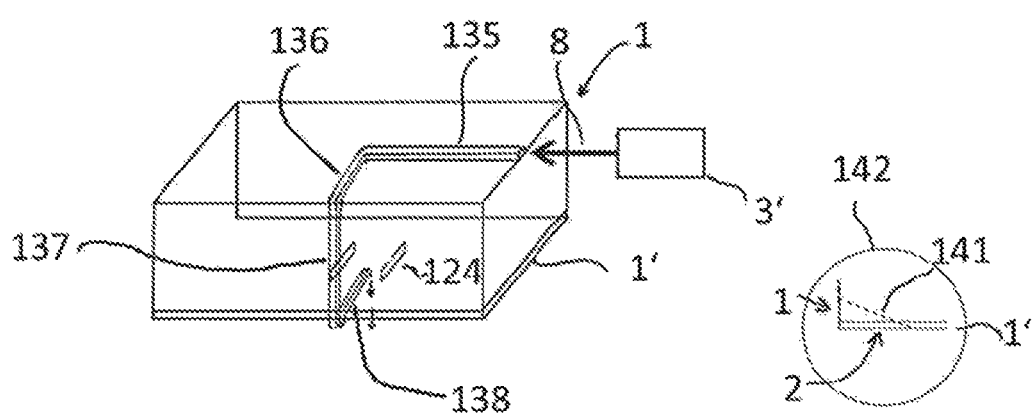

As can be seen from FIG. 26, an optical waveguide 135, 136, 137, 138 can also be provided to guide the excitation beam 8, which is guided, for example, in multiple directions and/or in two or three mutually perpendicular directions on one or two or three different, mutually adjacent surfaces of the measuring body 1. For example, such an optical waveguide 135, 136, 137, 138 can be integrated into the respective measuring body 1, as can the optical waveguides shown in FIGS. 24 and 25. On the surfaces of a measuring body, this is particularly simple to implement in SOI technology or, depending on the material of the measuring body, in a related solid-state manufacturing technology. In a silicon substrate, an optical waveguide can be incorporated for this purpose, which is covered and separated from the substrate by silicon oxide layers or other layers. To this end, a suitable recess can first be etched or sputtered into the substrate, in order to then appropriately deposit the material of the covering and the optical waveguide. In this case, for example, the covering of the optical waveguide can terminate flush with the surface of the measuring body so that the optical waveguide 135, 136, 137, 138 does not protrude beyond the measuring body 1. The course of the optical waveguide 135, 136, 137, 138 along the surfaces of the measuring body 1 prevents any interaction of the excitation beam 8 with the detection device and the effects of the piezoelectric material. The last optical waveguide 138 then ends in the region in which the excitation beam 8 should enter the substance to be analysed. At the end of the optical waveguide 138, an element can be provided that directs the excitation beam 8 into the substance, for example a mirror.

The detail shown in FIG. 26 in a circle 142 in the lower right corner of the figure shows that the optical waveguide 138 can also be arranged in a recess or groove (shown dotted) of the measuring body 1 leading diagonally onto the measuring surface 2, so that the longitudinal axis of the optical waveguide is directed parallel to the bottom 141 of the groove through the measuring surface 2 onto the substance to be analysed.

The present patent application relates (as already mentioned at the outset) to the following aspects in addition to the subject matter of the claims and exemplary embodiments described above. These aspects, or individual features thereof, can be combined with features of the claims, either individually or in groups. The aspects also constitute independent inventions, whether taken in isolation or combined with one another or with the subject matter of the claims. The applicant reserves the right to make these inventions the subject of claims at a later date. This may take place within the scope of this application or in the context of subsequent part applications or subsequent applications, claiming the priority of this application.

Aspects

1) Method for analysing a substance in a body, comprising:
    emitting an excitation light beam (excitation beam) with one or more specific excitation wavelengths through a first region of the surface of the body,
    intensity modulation of the excitation light beam with one or more frequencies, in particular sequentially, by means of a mechanical, electrical or optical chopper, in particular by an electronic activation of the excitation light source, an adjustment device for a resonator of an excitation laser acting as an excitation light source or a movable mirror device, a controllable diffraction device, a shutter or mirror device coupled to a motor, such as a stepper motor, or to a MEMS, or a layer in the beam path that can be controlled with respect to transmission or reflection,
    a time-resolved detection of a response signal that is due to the effect of the wavelength-dependent absorption of the excitation light beam in the body by means of a detector arranged outside the body.

The detector may be formed, for example, by an optical medium/measuring body with a detection region, which is in particular adjacent to or directly adjacent to the measuring surface (=boundary surface of the measuring body in contact with the substance to be analysed), and which has a pressure- or temperature-dependent specific electrical resistance and/or generates electrical, particularly piezoelectric, voltage signals in the event of pressure or temperature changes, and with an electrical contact device which has electrodes that are electrically conductively connected to the detection region of the optical medium/measuring body for detecting the electrical resistance and/or the electrical signals, wherein a detection device is formed with the contact device and the detection region.

For example, the detector/detection device can comprise a piezoelectric material or a temperature-dependent resistance with a positive or negative temperature coefficient (thermistor) or a thermocouple.

The modulation can be carried out in one embodiment by interference or by manipulating the phase or polarization of the radiation of the excitation transmission device, in particular if this comprises a laser light device. The modulation can also be performed by controlling an actively operated piezoelement, which is a part/element of the measuring body and the transmission or reflection property/reflectivity of which can be controlled by a voltage controller on the piezoelement. The response signals can be, for example, intensities or deflection angles of a reflected measurement beam or voltage signals of a detector operating with a piezoelectric effect.

2) Method according to aspect 1, characterized in that the excitation light beam/excitation beam is generated by a plurality of emitters or multi-emitters, in particular in the form of a laser array, which emit light at different wavelengths simultaneously or sequentially or in pulse patterns, or also alternately.

3) Method according to aspect 1 or 2, characterized in that an acoustic response signal is detected by an acoustic sensor at the first region of the surface of the body.

4) Method according to any one of aspects 1 to 3, characterized in that at the first region of the surface of the body, a response signal is detected by an infrared radiation sensor, in particular a thermocouple, a bolometer or a semiconductor detector, such as a quantum cascade detector, or a piezo-detector. The piezo-detector can be formed, for example, in or on a measuring body/optical medium.

5) Method according to any one of aspects 1 to 4, comprising the steps:
    establishing the contact of an optical medium/measuring body with a substance surface of the body, so that at least one region of the surface of the optical medium/measuring body (e.g. a measuring surface) is in contact with the first region of the surface of the body;

emitting an excitation light beam with an excitation wavelength into a volume located in the substance below the first region of the surface, in particular through the region of the surface of the optical medium which is in contact with the first region of the substance surface, measuring the temperature or temperature change and/or a pressure change in the first region of the optical medium surface by an optical pyrometric or photothermic method;

analysing the substance on the basis of the detected temperature increase as a function of the wavelength of the excitation light beam. This process can be performed during one measurement for different modulation frequencies and the results for different modulation frequencies can be combined.

6) Method according to aspect 5, characterized by the emission of a measurement light beam through the optical medium/measurement body onto the region of the surface of the optical medium, which is in direct contact with the substance surface, in such a manner that the measurement light beam and the excitation light beam are directly adjacent to each other or overlap at an interface of the optical medium/measurement body and the substance surface at which the measurement light beam is reflected;

direct or indirect detection of a deflection of the reflected measurement light beam as a function of the wavelength of the excitation light beam and analysing the substance on the basis of the detected deflection of the measurement light beam as a function of the wavelength of the excitation light beam. This process can be performed during one measurement for different modulation frequencies and the results for different modulation frequencies can be combined.

This method can also be used, for example, with a flat measuring body and lateral irradiation of the excitation beam (substantially parallel to the measuring surface), and with the excitation beam being reflected to the measuring surface and to the substance to be analysed.

7) Method according to any one of aspects 5 or 6, characterized in that the measuring light beam is generated by the same light source that generates the excitation light beam.

8) Method according to any one of aspects 5, 6 or 7, characterized in that the measurement beam is reflected one or more times within the optical medium, outside the optical medium, or partly inside and partly outside the optical medium after deflection and before detection.

9) Method according to aspect 1 or any of the others preceding or following, characterized in that the excitation light beam is an intensity-modulated, in particular pulsed excitation light beam, in particular in the infrared spectral range, wherein the modulation rate is in particular between 1 Hz and 10 kHz, preferably between 10 Hz and 3000 Hz.

10) Method according to aspect 1 or any of the others preceding or following, characterized in that the light of the excitation light beam(s) is generated simultaneously or sequentially or partially simultaneously and partially sequentially, by means of an integrated arrangement having a plurality of individual lasers, in particular a laser array.

11) Method according to aspect 1 or any of the others preceding or following, characterized in that an intensity distribution of the response signals is determined from the response signals obtained at different modulation frequencies of the excitation light beam as a function of the depth below the surface at which the response signals are generated.

12) Method according to aspect 1 or any of the others preceding or following, characterized in that an intensity distribution of the response signals is determined from the phase offset of the response signals in relation to a modulated excitation light beam at one or different modulation frequencies of the excitation light beam, as a function of the depth below the surface at which the response signals are generated.

13) Method according to aspect 11 or 12, characterized in that to determine the intensity distribution of the response signals as a function of the depth below the surface, the measurement results at different modulation frequencies are weighted and correlated with each other.

14) Method as claimed in aspect 11, 12 or 13, characterized in that a material density of a substance that absorbs the excitation light beam in specific wavelength ranges at a specific depth or in a depth range is determined from the intensity distribution over the depth below the surface of the body.

15) Method according to aspect 1 or any of the others preceding or following, characterized in that immediately before or after or during the detection of the response signal/signals, at least one biometric measurement is carried out on the body in the first region of the surface in which the substance analysis is performed or directly adjacent thereto, in particular a measurement of a fingerprint, and the body, in particular a person, is identified and that, in particular, associated reference values (calibration values) are assigned to the detection of the response signals by the identification of the person.

The biometric measurement can also include the measurement of a spectrum of response signals when scanning over a spectrum of the excitation light beam. By evaluation of the spectrum, a profile of substances present in the body and their quantity or density ratio can be determined, which can enable the identification of a person.

16) Device for analysing a substance, having a device for transmitting one or more excitation light beams, each of which has an excitation wavelength, into a volume located in the substance below a first region of its surface, with a device for modulating an excitation light beam which is formed by a modulating device of the radiation source, in particular the control thereof, an interference device, a phase or polarization modulating device and/or at least one controlled mirror arranged in the beam path, and/or a layer that can be controlled with regard to its transparency and arranged in the beam path, and having a detection device for detecting a time-dependent response signal as a function of the wavelength of the excitation light and the intensity modulation of the excitation light, and having a device for analysing the substance using the detected response signals.

17) Device according to aspect 16, having a device for determining response signals separately according to different intensity modulation frequencies and/or having a device for determining response signals as a function of the phase offset of the respective response signal relative to the phase of modulation of the excitation light beam, in particular as a function of the modulation frequency of the excitation light beam.
18) Device for analysing a substance as defined in 16 or 17, having an optical medium/measuring body for making the contact between the surface of the optical medium (for example, a so-called measuring surface) and a first region of the substance surface, and having a device for emitting an excitation light beam with one or more excitation wavelengths into a volume located in the substance below the first region of the surface, in particular through the region of the surface of the optical medium (the measuring surface) which is in contact with the surface of the substance, and having a device for
measuring response signals in the form of temperature and/or pressure changes in the region within the measuring body in the immediate vicinity of the measuring surface (a so-called detection region), which is in contact with the first region of the material surface, by means of an optical procedure that makes use of a measurement light beam or by means of the method described above using a piezo-effect, and having a device for analysing the substance using the detected response signals in the form of temperature changes/pressure changes as a function of the wavelength of the excitation light beam and the intensity modulation of the excitation light beam, in particular the modulation frequency of the excitation light beam.

In this aspect and the following aspects relating to it, it may also be provided for the measuring body to have a first part that has a recess/slot in the form of a continuous channel for the excitation beam and that the measuring body on its underside has a sensor layer on the first part, which is either continuous without a recess/slot for the excitation beam or is provided with a continuation of the recess of the first part. If the sensor layer is thin enough, for example thinner than 200 microns, in particular thinner than 100 microns, then depending on the selected material of the layer the excitation beam, even if it is an infrared beam, can also pass through without too much absorption and a recess/slot in the sensor layer is not necessary. The sensor layer of the measuring body can be adhesively bonded to the first part/remainder of the measuring body or be joined to it by another joining technique, and can consist of a material that has piezoelectric properties and forms a detection region according to the invention. The sensor layer can also consist of a material in which a change in temperature and/or pressure causes a change in the refractive index, so that this change can also be detected as a response signal, for example by detecting the angle of reflection of a detection beam that is reflected in or on the sensor layer. For example, the first part/remainder of the measuring body can then consist of a material which is permeable in the visible range and for a detection beam, but is less permeable or impermeable in the infrared spectral range, such as quartz or sapphire or a plastic, for example a polymer.

Figure 17:
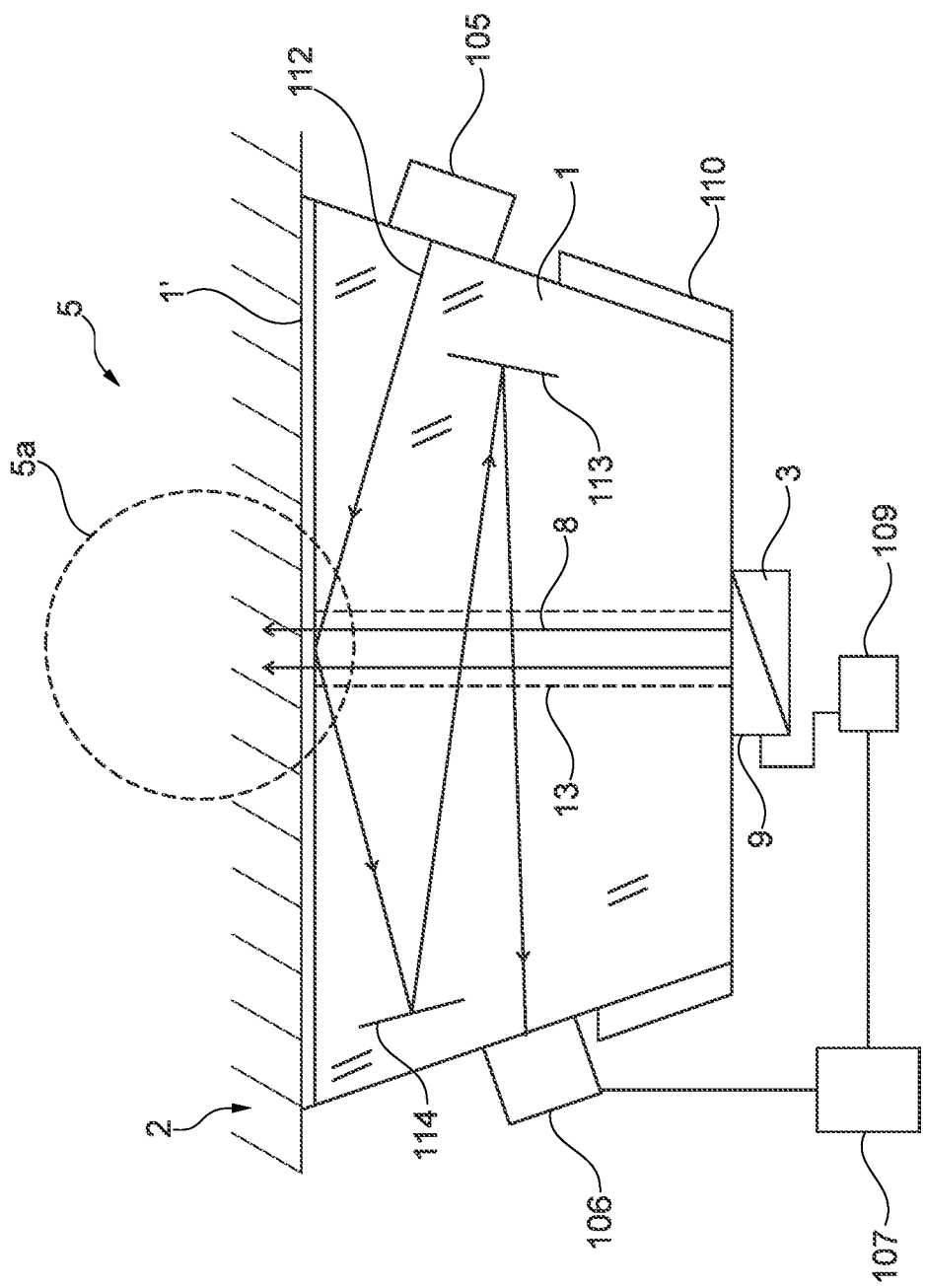
FIG. 17 shows a design of the invention with a detection device that detects the reflection of a measurement light beam.

19) Device according to aspect 18, characterized in that the excitation light source is directly permanently mechanically connected to the optical medium/measuring body.
20) Device according to aspect 18, characterized in that a device is provided for transmitting a measuring light beam into the region of the optical medium/measuring body that is in contact with the first region of the surface of the substance and that this device/or the detection device for detecting the measuring light beam is permanently directly mechanically connected to the optical medium/measuring body, integrated into it or coupled to it by means of an optical waveguide.
21) Device according to aspect 18, 19 or 20, characterized in that the optical medium/measuring body directly carries an imaging optics and/or that an imaging optics is integrated into the optical medium/measuring body.
22) Device according to aspect 18 or any of the others preceding or following, characterized in that the surface of the optical medium/measuring body has a plurality of partial faces inclined towards one another, at which the measuring light beam is reflected multiple times.
23) Device according to aspect 18 or any of the others preceding or following, characterized in that in or on the optical medium/measuring body, one or more mirror surfaces are provided for the reflection of the measuring light beam.
24) Due to the multiple reflection of the measurement beam, the path of the beam is extended so that angular deviations can be better detected (see also FIG. 17).
25) Device according to aspect 16 or 17, characterized in that the detection device for detecting a time-dependent response signal has an acoustic detector for detecting acoustic waves on the surface of the material, in particular with a resonator, more particularly with a Helmholtz resonator.

Independently of this, a quartz tuning fork with preferably the same resonance frequency as a designated resonator can be used as a detector. The resonator can be open or closed. The quartz fork is preferably located in or on the neck of the resonator (off-beam) or inside/outside the resonator (in-beam).

26) Device according to aspect 16, 17 or 18, characterized in that the detection device for detecting a time-dependent response signal has a heat radiation detector for detecting the heat radiation on the surface of the substance, in particular an infrared detector, more particularly a thermocouple, a bolometer, or a semiconductor detector or a piezoelement.
27) Device according to any one of aspects 16 to 25, characterized in that the excitation light source and the detection device are attached directly to each other or to a common carrier, which is formed in particular by a housing or housing part of the device.
28) Device according to any one of aspects 16 to 26, characterized in that the device has a portable housing which can be attached to a person's body, wherein the device for emitting one or more excitation light beams and the detection device for detecting a time-dependent response signal are arranged and configured in such a manner that in operation, if the device is worn on the body, the substance to be analysed is measured on the side of the housing facing away from the body, in particular that the measuring surface of the measuring body is located on the side facing away from the body.
29) Device according to any one of aspects 16 to 26, characterized in that the device has a portable housing that can be attached to the body of a person and that the housing of the device has a window that is permeable to the excitation beam on its side facing away from the body at the intended wearing position.

The window can be located directly in front of the measuring body or be formed by the measuring surface of the measuring body.

29a) Device for analysing a substance with an excitation emission device for generating at least one electromagnetic excitation beam, in particular excitation light beam, with at least one excitation wavelength, a detection device for detecting a response signal and a device for analysing the substance using the detected response signal.

30) Device according to any one of the preceding aspects 16 to 29a, characterized in that the detection device is configured to measure the deformation of a crystal or other material transparent in the visible region of the spectrum.

The deformation can be measured more effectively by selecting steeper (larger) angles of incidence of the measurement beam to the sample surface, analogously to the photothermic 'bouncing method', and the deflection of the measurement beam caused by the mirage effect can be minimized.

Literature:

M. Bertolotti, G. L. Liakhou, R. Li Voti, S. Paolino, and C. Sibilia. Analysis of the photothermal deflection technique in the surface refection theme: Theory and Experiment. Journal of Applied Physics 83, 966 (1998)

A cantilever can either be placed directly on the sample or on a sufficiently thin optical medium on which the sample is placed on one side and the cantilever is placed on the opposite side. The thermal expansion of the sample or optical element causes the cantilever to vibrate as a result of the thermal expansion caused by the absorption of the modulated pump beam/excitation beam. The measurement beam is reflected at a measuring surface of the cantilever and is deflected by the vibration as a function of the irradiated wavelength and the thermal properties of the sample, as well as the modulation frequency. This deflection is detected.

31) Device according to any one of the preceding aspects 16 to 30, characterized in that the excitation transmission device contains a probe laser or an LED, such as a NIR (near-infrared) LED.

32) Device according to any one of the preceding aspects 16 to 31, characterized in that the excitation transmission device has a probe laser that has a smaller diameter than an additional pump laser (=laser for generating the excitation beam).

33) Device according to any one of the preceding aspects 16 to 32, characterized in that to achieve a more favourable signal-to-noise ratio, a special coating is provided, in particular on the emitter, e.g. IRE, so that heat is better dissipated (e.g. "thermal conductive paste").

The optical element can be coated on the contact surface in such a manner that an improved conduction of the thermal signal into the optical medium can take place. In addition, the coating can also be used as scratch protection, and by skillful material selection can also provide a reflective surface for the measurement beam. In this case it is mandatory to retain the transparency for the excitation light.

34) Device according to any one of the preceding aspects 16 to 33, characterized in that the device has a system for
i. pulse trains/double modulation
ii. oscillating mirror
iii. MEMS interferometer.

35) Device according to any one of the preceding aspects 16 to 34, characterized in that the device is designed to be permanently wearable for a person on the body, in one embodiment by means of a retaining device connected to the housing, such as a belt, a strap or a chain or a clasp, and/or the detection device has a detection surface which also serves as a display surface for information such as measurements, times of day and/or textual information.

The detection surface can be identical to the measuring surface or form its extension/continuation.

36) Device according to the previous aspect 35, characterized in that the device has a peel-off film in the region of the detection surface/measuring surface, preferably next to the detection surface/measuring surface, for pre-treatment of the surface of the substance and ensuring a clean surface and/or in one embodiment in the case of glucose measurement, specifically for skin cleansing.

37) Device according to any one of the preceding aspects 16 to 36, characterized in that The detection device is configured for reading and recognizing fingerprints to retrieve specific values/calibrations of a person and/or that it has a device for detecting the position of a finger, preferably for detecting and determining an unwanted movement during the measurement.

38) Device according to any one of the preceding aspects 16 to 37, characterized in that the detection device has a result display, preferably implemented with colour coding, as an analogue display, in one embodiment including error indication (e.g.: "100 mg/dl plus/minus 5 mg/dl"), acoustically and/or with a result display of measurement values in larger steps than the measuring accuracy of the device allows (e.g. using a multi-coloured traffic light display). This means that the user is not informed of small fluctuations, which could cause uncertainty for them.

39) Device according to any one of the preceding aspects 16 to 38, characterized in that the device
has data interfaces for exchanging measured data and for retrieving calibration or identification data or other data from other devices or cloud systems, for example, wired or wireless interfaces (infrared, light or radio interfaces),
wherein the device is preferably configured to ensure that data transmission can be encrypted, in particular encrypted by fingerprint or other biometric data of the operator.

40) Device according to any one of the preceding aspects 16 to 39, characterized in that the device is configured such that a proposal for an insulin dose or substances/foodstuffs to be given to the person and the quantity to be consumed can be determined by the device (e.g. insulin correction factor) and/or that the body weight, body fat can be measured and/or entered manually or transferred from other devices to the device at the same time.

41) Device according to any one of the preceding aspects 16 to 40, characterized in that to increase the measuring accuracy the device is configured to determine further parameters, in one embodiment by means of sensors for determining the skin temperature, diffusivity/conductivity/moisture level of the skin, for measuring the polarization of the light (excluding water/sweat on the finger surface).

Water and sweat on the surface of a person's skin, which can affect the glucose measurement, can be detected by a test excitation with an excitation radiation by means of the excitation transmission device with the water-specific bands at 1640 cm$^{-1}$ (6.1 μm) and 690 cm$^{-1}$ (15 μm). If the absorption exceeds a certain value, the measurement site/substance surface/skin surface is too wet for a reliable measurement. Alternatively, the conductivity of the substance can be measured near to or directly at the measuring site to determine the moisture level. An error message and a drying instruction can then be issued.

42) Device according to any one of the preceding aspects 16 to 41, characterized in that the device is provided with a cover in the beam path of the pump and/or measurement beam laser. This can ensure the obligatory eye safety of human beings.

43) Device according to any one of the preceding aspects 16 to 42, characterized in that the device has a replaceable detection surface/measuring surface.

44) Device according to any one of the preceding aspects 16 to 43, characterized in that the device as an optical medium/measuring body has a partially grooved or roughened crystal as a measuring body, which enables the sample (e.g. the finger) to be better calibrated. The measuring point on which the surface of the substance to be analysed is placed is preferably designed without grooves and smooth.

45) Device according to any one of the preceding aspects 16 to 44, characterized in that a cylindrical TEMp1 TEM00 mode is used for the measurement beam, or other modes TEM01 (Doughnut), TEM02 or TEM03 instead of the cylindrical TEMp1 TEM00 mode. The latter, in particular, have the advantage that their intensity can be matched to the sensitivity profile of the quadrant diode, which forms the detector for the deflected measurement beam. In addition, rectangular TEMmn modes, such as TEM30 or TEM03 or higher, can be used. This allows the use of scanning/measurement beams that are less sensitive to interference in the horizontal or vertical direction.

46) Device according to any one of the preceding aspects 16 to 45, characterized in that the device measures not only at one point, but in a grid. This can be carried out either by displacing the pump or probe laser or the detection unit relative to the skin surface of a subject. Instead of a displacement, it is also conceivable to use one or more arrays of pump or probe lasers, which are spatially distributed across the array.

In addition, the following aspects of the invention must also be cited:

47) Device (10) for analysing a substance, in particular also according to any one of claims 16 to 46, having
an excitation transmission device/laser device for generating at least one electromagnetic excitation beam, in particular excitation light beam, with at least one excitation wavelength,
a detection device for detecting a response signal and
a device for analysing the substance using the detected response signal.

The time-dependent response signal can take the form of the temperature or pressure increase in the measuring body as well as of any measured variable that detects the same, for example in the deflection of a measurement beam or an electrical signal of a piezoelement located in or on the measuring body.

48) Device according to aspect 47, (reference signs refer to FIG. 17), characterized in that
the excitation transmission device is a radiation source 3, in one embodiment a monochromatic, in particular a polarized radiation source, more particularly a laser light source,
the device has an optical medium/measuring body 1, 1', which is in direct contact with the substance 5, in particular a first region 5a of the surface of the substance (the measuring body may be homogeneous overall and composed of a material, the refractive index of which changes with the temperature, or at least in the region of the measuring surface it can have a layer 1' of such material, or a layer in which the refractive index changes more strongly as a function of temperature than in the other regions of the measuring body),
wherein the excitation transmission device is preferably arranged such that the emitted excitation beam 8 passes through the optical medium/measuring body 1, 1' (not necessarily the material of the measuring body) and leaves the limits of the measuring body at the surface of the optical medium/measuring surface again, and
the device comprises a device 105 for emitting a measurement beam, in particular a measurement light beam 112, arranged in such a way that the emitted measurement beam penetrates the optical medium and wherein in operation the measurement beam and the excitation beam preferably overlap at an interface/measuring surface 2 of the optical medium and the surface of the substance at which the measurement beam (112) is reflected (this region can be identical or partially identical to the measuring surface) and
the detection device is a device 106 for receiving the reflected measurement beam 112 forming the response signal and/or for directly or indirectly detecting a deflection of the reflected measurement beam.

It may also be provided that the excitation transmission device 3 comprises more than two transmitting elements in the form of lasers, in particular in the form of a one-, two- or multi-dimensional transmission element arrays, and that the fixed wavelengths of the electromagnetic excitation beams of the two or more transmitting elements differ, and
a modulation device is provided for intensity modulation of the excitation beam, and that
a detection device for detecting a response signal is provided and
a device 107, 109 for analysing the substance on the basis of the detected response signal,
wherein the measuring body consists of a material transparent to the measurement beam, in particular glass, crystal or a transparent plastic, wherein the detection device is a device 106 for receiving the measurement beam forming the response signal, which is reflected one or more times (according to FIG. 17, except in layer 1', also at two other reflection elements 114, 115 for extending the beam path) within the measuring body, and/or for directly or indirectly detecting a deflection of the reflected measurement beam, and the device for emitting a measurement beam and the detection device are aligned relative to each other in such a way that the detection device detects the measurement beam as the time-dependent response signal after said beam has been reflected at least once in the region of the measuring surface of the optical medium/measuring body. The detection device 106 can have a location-sensitive photoelectric detection element, for example a quadrant diode, which is located in the beam path of the measurement light beam behind the reflection point located on the measuring surface and detects the position of the measurement beam.

The detection device is therefore suitable for detecting a time-dependent response signal as a function of the wavelength of the excitation light and/or the intensity modulation of the excitation light. For this purpose, the evaluation unit 109 is also connected to a modulation device 9 for the excitation beam. Furthermore, the device is suitable for analysing the substance based on the detected response signal, wherein using different modulation frequencies of the excitation transmission device, response signals, in particular temporal response signal waveforms for different wavelengths of the excitation beam, are successively determined and a plurality of response signal waveforms at different modulation frequencies are correlated by the evaluation device 109 and that from this, information specific to a depth range below the substance surface is obtained.

For the embodiments according to aspects 47 or 48 also, it is conceivable to design the measuring body as a flat body, with a thickness/dimension perpendicular to the measuring surface which can be less than 50%, in particular less than 20%, more particularly less than 10% of the smallest dimension of the measuring body parallel to the measuring surface. The excitation transmission device/laser device for generating the excitation beam can then be positioned and aligned to the side of the measuring body in such a way that it emits the excitation beam into the measuring body substantially parallel to the measuring surface (or with an angular deviation of less than 20 degrees from this direction). (This may require that the excitation beam be coupled out of the excitation transmission device into an optical waveguide and from there into the measuring body. However, a mirror device may also be provided between the excitation transmission device/laser device and the measuring body, so that the excitation beam emerging from the excitation transmission device is initially reflected by a first mirror in the direction of a lateral, imaginary extension of the measuring surface and then diverted in a direction parallel to the measuring surface). The excitation beam can then be redirected to the measuring surface and from there enter the substance to be analysed.

49) Device according to either of the aspects 47 or 48,
characterized in that
the device has an optical medium/measuring body which is in direct contact with the substance, in particular a first region of the surface of the substance, and that for detecting a response signal the detection device detects a change in a parameter of the optical medium/measuring body, in particular in a region adjacent to the first region, as a result of the response signal, in particular, a deformation and/or density change or a change in the refractive index of the optical medium.

In the devices of the above-mentioned type, in particular in the devices in accordance with aspects 47, 48 or 49, it can also be provided that the measuring body is coated in the region of the measuring surface with a material which changes its refractive index more strongly as a function of temperature or pressure than the rest of the measuring body, the coating being advantageously thinner than 1 mm, more advantageously thinner than 0.5 mm, in particular thinner than 0.2 mm or thinner than 0.1 mm. The coating can also be formed as an adhesively bonded sensor layer or one which is attached to a remaining/first part of the measuring body.

In the remaining part of the measuring body, which is connected to the coating or sensor layer, a recess 13 (cf. FIG. 17) can be introduced in such a manner that the excitation beam in this region of the measuring body does not touch or pass through the material of at least a first part of the measuring body. The remaining region of the measuring body must be permeable to the measurement beam, i.e. permeable in the visible range of the spectrum, so that this measurement beam can reach the coating/sensor layer and be reflected thereon or therein.

The material of the measuring body, which is connected to the coating/sensor layer 1' (see also FIG. 17), can have a specific thermal capacity or thermal conductivity greater than that of the material of the coating 1', so that the remaining part of the measuring body that connects to the coating can act as a heat sink for the coating. Alternatively or in addition, an additional heat sink or a Peltier element 110 can also be provided on the measuring body, by means of which the temperature of the measuring body can be controlled using a control device.

In this case, the reflection angle of the measurement beam represents the response signal to be detected.

50) Device according to any one of the aspects 47, 48 or 49,
characterized in that
the detection device has a piezoelement connected to or integrated into the optical medium as a detector for detecting the deformation and/or temperature or density change.

51) Device according to aspect 47 or any one of the following,
characterized in that the detection device has temperature sensors as a detector for detecting the response signal.

52) Device according to aspect 47 or any one of the following,
characterized in that
the device has a device for intensity modulation of the excitation light beam, and
the detection device is suitable for detecting a time-dependent response signal as a function of the wavelength of the excitation light and/or the intensity modulation of the excitation light.

53) Device according to aspect 47 or any one of the following,
characterized in that
to generate the excitation beam the excitation transmission device/laser light source emits the at least one electromagnetic excitation beam into a volume of substance that lies underneath a first region of the surface of the substance.

54) Device according to aspect 47 or any one of the following,
characterized in that
the excitation transmission device/laser light source for generating the excitation beam comprises two or more transmitting elements, in particular in the form of a one-, two- or multi-dimensional transmission element array.

The individual transmitting elements can be QC lasers or solid-state lasers with a fixed wavelength, for example.

55) Device according to aspect 47 or any one of the following,
characterized in that
the two or more transmitting elements each generate a separate electromagnetic excitation beam and radiate it into the volume below the first region.

56) Device according to aspect 47 or any one of the following,
characterized in that
the wavelengths of the electromagnetic excitation beams of the two or more transmission elements differ.

57) Device according to aspect 47 or any one of the following,
characterized in that
the excitation transmission device/laser light source for generating the excitation beam comprises two or more lasers, in particular in the form of a one- or two-dimensional laser array, and/or two or more LEDs, in particular in the form of a one-, two- or multi-dimensional diode array.

58) Device according to aspect 47 or any one of the following,
characterized in that
the excitation transmission device is directly—or indirectly by means of a calibration device—connected to an optical medium/measuring body, which is permanently mechanically connected to the substance, in particular the first region of the surface of the substance in which the measurement is performed to analyse the substance.

59) Device according to aspect 47 or any one of the following,
characterized in that
the intensity modulation device comprises or is formed by an electrical modulation device that is electrically connected to and electrically controls the excitation transmission device/laser light source to generate the excitation beam.

60) Device according to aspect 47 or any one of the following,
characterized in that
the intensity modulation device comprises at least one controlled mirror arranged in the beam path.

61) Device according to aspect 47 or any one of the following,
characterized in that
the intensity modulation device comprises or is formed by at least one layer, controllable with regard to its transparency, arranged in the beam path.

62) Device according to aspect 47 or any one of the following,
characterized in that
a device (105) is provided for emitting a measurement beam, in particular a measurement light beam, into the region of an optical medium/measuring body which is in contact with the surface of the substance on which the material analysis is performed. The corresponding surface of the measuring body is also called the measuring surface.

63) Device according to aspect 47 or any one of the following,
characterized in that
the device for emitting a measurement beam and the detection device are aligned relative to each other in such a way that the detection device detects the measurement beam as the time-dependent response signal after the former has been reflected at least once at the interface of the optical medium (=the measuring surface) that is in contact with the substance, in particular the first region of the surface of the substance.

The measuring surface can be the outer surface of a sensor layer that forms part of the measuring body and is connected to the remainder of the measuring body, in particular by adhesive bonding.

64) Device according to aspect 47 or any one of the following,
characterized in that
the device for emitting a measurement beam and/or the detection device and/or excitation transmission device is mechanically permanently connected to the optical medium/measuring body and/or coupled thereto by means of an optical waveguide.

65) Device according to aspect 47 or any one of the following,
characterized in that
the optical medium/measuring body directly carries an imaging optics and/or an imaging optics is integrated into the optical medium. For example, the imaging optics can contain one or more lenses or reflective surfaces moulded into the measuring body. For example, the surface of the measuring body can be shaped as a lens for this purpose.

66) Device according to aspect 47 or any one of the following,
characterized in that
the surface of the optical medium has a plurality of partial faces inclined towards one another, at which a measurement beam, in particular the measurement light beam, is reflected multiple times.

67) Device according to aspect 47 or any one of the following,
characterized in that
in or on the optical medium/measuring body, one or more mirror surfaces are provided for the reflection of the excitation beam or a measurement beam, in particular measurement light beam.

68) Device according to aspect 47 or any one of the following,
characterized in that
the excitation transmission device (and/or the device for emitting the measurement beam and/or the detection device) are attached directly to each other or to a common carrier. This carrier can be movable in a controlled manner as a unit relative to the measuring body and can be adjusted relative to it by means of a calibration device.

69) Device according to aspect 47 or any one of the following,
characterized in that
the carrier is formed by a printed circuit board, a metal plate or plastic plate, or a housing or housing part of the device.

70) Device according to aspect 47 or any one of the following,
characterized in that
the excitation transmission device comprises an integrated semiconductor device that has one or more laser elements as well as at least one micro-optical component and preferably an additional modulation element.

71) Device according to aspect 47 or any one of the following, characterized in that
the modulation element has at least one element, in particular a mirror, which is movable relative to the rest of the semiconductor component and controllable in relation to its position.

72) Device according to aspect 47 or any one of the following,
characterized in that
the modulation element has a layer that can be controlled in terms of its radiation transmittance.

73) Device according to aspect 47 or any one of the following,
characterized in that
the modulation element has an electronic control circuit for modulating the one or more laser elements.

74) Device according to any one of the previous aspects, characterized in that the measuring body or optical medium is formed as a flat body, in particular as a plane-parallel body in the form of a plate, wherein in particular the thickness perpendicular to the measuring surface (in other words, the boundary surface of the optical medium on which the substance to be analysed is placed) is less than 50% of the smallest expansion of the measuring body in a direction parallel to the measuring surface, in particular less than 25%, more particularly less than 10% or less than 5% or less than 1%.

An imaging optics may be mounted on a surface adjacent to or opposite to the measuring surface, or on the measuring surface itself, or an imaging optics may be integrated into this surface. The imaging optics can contain at least one lens.

75) Device according to any one of the previous aspects, characterized in that the measuring body/optical medium has or carries a mirror device to reflect the excitation beam emitted by the laser device to the measuring surface (or the interface of the optical medium on which the substance to be analysed is placed).

76) Device for analysing a substance according to claim 1 or any one of the following, characterized in that the excitation beam is irradiated into the measuring body parallel to the measuring surface (or the boundary surface of the optical medium on which the substance to be analysed is placed) or at an angle of less than 30 degrees, in particular less than 20 degrees, more particularly less than 10 degrees or less than 5 degrees to the measuring surface (or the boundary surface of the optical medium on which the substance to be analysed is placed) and that the excitation beam is diverted or deflected towards the measuring surface (or the interface of the optical medium on which the substance to be analysed is placed) and passes through it.

The measuring body can have a channel-like recess for the excitation beam, the longitudinal direction of which runs parallel to the measuring surface, so that the distance that the excitation beam travels in the material of the measuring body until it exits through the measuring surface is reduced, in particular, reduced to zero. If a sensor layer is integrated into the measuring body, the recess/slot in the measuring body can reach as far as this.

77) Method for analysing a substance, wherein in the method
using an excitation transmission device, at least one electromagnetic excitation beam with one or more excitation wavelengths is generated and transmitted into the substance by the at least partially simultaneous or consecutive operation of a plurality of laser emitters of a laser light source,
a response signal is detected with a detection device, and
the substance is analysed on the basis of the detected response signal.

78) Method according to aspect 77, characterized in that using different modulation frequencies of the excitation transmission device, response signals, in particular temporal response signal waveforms, are successively determined and that a plurality of response signal waveforms at different modulation frequencies are correlated with each other and that from this, information specific to a depth range below the surface of the substance is obtained.

79) Method according to aspect 78,
characterized in that
response signal waveforms at different modulation frequencies are determined for different wavelengths of the excitation beam and, in particular, from this information specific to a depth range below the surface of the substance is obtained.

80) Method according to aspect 79,
characterized in that
when using multiple modulation frequencies of the excitation beam at the same time, the detected response signal is separated according to its frequencies by means of an analysis method, preferably a Fourier transform, and
only one partial signal at a time is filtered, measured and analysed that corresponds to a frequency to be processed.

In this way, a plurality of signals at different modulation frequencies can be analysed successively and the results of different modulation frequencies can be correlated with one another to obtain depth information about the signals, or to eliminate signals coming from the surface of the substance.

81) Method according to any one of the preceding aspects 77 to 80,
characterized in that
an optical medium/measuring body is brought into direct contact with the substance, in particular a first region of the surface of the substance,
using the excitation transmission device the emitted excitation beam is generated and, in particular, radiated in such a way that it penetrates the optical medium and exits it again at a predetermined point on the surface of the optical medium, especially at a measuring surface,
a measurement beam, in particular a measurement light beam, is generated by means of a device for emitting a measurement beam, in such a way that said beam penetrates into the optical medium/measuring body and that, in particular, during operation the measurement beam and the excitation beam overlap at an interface of the optical medium and the surface of the material at which the measurement beam is reflected, in particular at the measuring surface, and
a reflected measurement beam forming the response signal is measured with the detection device
and/or the deflection of the reflected beam is detected directly or indirectly.

The reflected measurement beam can be measured, for example, by detecting its intensity with a spatially-resolving, light-sensitive semiconductor device, in particular a quadrant diode.

82) Method according to any one of the preceding aspects 77 to 81, characterized in that as a function of a concentration of the substance determined in the substance, a dosing device is activated to release another substance into the substance, in particular into a patient's body, and/or an acoustic and/or optical signal is emitted and/or a signal is issued to a processing device via a radio link and/or that one or more foodstuffs or foodstuff combinations are assigned to the measured substance concentration by means of a database and output as nutritional information, in particular as a nutritional recommendation.

In addition to or in combination with such a recommendation, a quantity indication can also be given for the foodstuffs or foodstuff combinations. Foodstuff combinations is also intended to mean prepared food portions.

All features and measures of the excitation beam, its optical guidance and modulation which are mentioned in the aspects in connection with any given measuring method, in particular in connection with a measurement light beam and the detection of its deflection, as well as the features of the mechanical structure and the adjustability, the features of the housing and the communication with external devices, databases and connected devices can also be applied to the detection method as claimed in the patent claims of the present application, i.e. using a piezoelectric effect to detect the thermal wave emitted from the substance into a measuring body as a response signal.

Other detection methods for detecting a response signal after emission of an excitation beam can comprise:

photoacoustic detection—photoacoustic detection by means of a tuning fork or other vibration element or: a slightly modified form of photoacoustics with open QePAS cell (Quartz-enhanced PhotoAcoustic Spectroscopy). These methods can be used to detect pressure fluctuations/vibrations on the surface of the substance and to evaluate them as described above for the measured beam deflection.

In principle, values of a phase shift of the response signal determined for depth profiling in response to a periodic modulation of the excitation beam can be used. (Heating/cooling phases of the substance surface should be evaluated more precisely with regard to their characteristics).

The device described may include a supply of adhesive strips for the removal of dead skin layers in order to allow the best possible interference-free measurement on a human body, as well as patches with thermal conductive paste, which can be regularly applied to the optical medium. The optical medium may be interchangeable given appropriate mounting and calibration of the remaining parts.

The device can be designed and configured for measurement not only on a person's finger, but also on a lip or earlobe.

The measurement can be improved by combining a number of the measurement systems described and explained with a similar susceptibility to error in terms of accuracy and reliability.

DAQ and lock-in amplifiers in the evaluation can be combined in one device and the entire evaluation process can be digitized.

The measurement can also be carried out with the device on a substance surface that is moving relative to the device, so that in the course of a grid measurement: the excitation light source and/or the measurement light source move across the skin in a grid pattern, allowing skin irregularities to be compensated or averaged out.

The sensitivity of the detection device/deflection unit can be optimized by adjusting/varying the wavelength of the sample beam/measurement light source. For this purpose, the measuring light source can be variable with respect to wavelength, or contain a plurality of laser light sources of different wavelength for selection or combination.

An optimum transversal mode (TEM) can be selected for the deflection of the pump/probe laser.

The excitation transmission device, measurement light source and detector can be assembled as a common array and the beams can be deflected in the optical medium in a suitable way to concentrate the transmission and reception of all beams on to one place.

A lens on or in the crystal of the optical medium can be used to deflect the measurement light beam more strongly depending on the response signal.

In addition, the use of a gap-free photodiode is conceivable for the detection, in which case a lens could focus the measurement light beam after its emission, thus enabling a more accurate measurement.

An additional configuration of the invention according to the patent claims is presented in the following concept. In addition, this concept, whether taken in isolation, combined with the above aspects or with the subject matter of the claims, constitutes at least one invention in itself. The applicant reserves the right to make this invention or inventions the subject of claims at a later date. This may take place within the scope of this application or in the context of subsequent part applications or subsequent applications, claiming the priority of this application.

The following concept for non-invasive blood sugar measurement by determining the glucose in the skin by stimulation by quantum cascade lasers and measuring the thermal wave due to radiant heat shall also be included in the invention and can be combined with the objects of the claims or pursued independently in a divisional application:

A method is described that allows the concentration of glucose or any other substance in the interstitial fluid (ISF) in the skin to be determined. Glucose in the ISF is representative of blood glucose and follows it rapidly when changes occur. The method consists of at least individual steps or groups of the following steps or from the overall sequence:

1. The point on the skin (in this case, the first region of the surface of the substance) is irradiated with a focused beam of a quantum cascade laser that may also be reflected at a mirror or concave mirror, and which is incrementally or continuously tuned over a specific infrared range in which radiation is absorbed glucose-specifically. Instead of the quantum cascade laser, a laser array having a plurality of lasers radiating with single wavelengths can also be used. The spectral range (or the individual wavelengths, typically 5 or more wavelengths) can be located between approximately 900 and approximately 1300 $cm^{-1}$, in which glucose has an absorption fingerprint, i.e. typical and representative absorption lines.

2. The excitation beam is used in a continuous mode (CW laser) or pulsed or modulated with a high pulse repetition rate. In addition, the excitation beam is modulated at low frequency, in particular in the frequency range between 10 and 1000 Hz. The low-frequency modulation can be performed with different periodic functions, in different embodiments with a sinusoid, a square wave or sawtooth wave.

3. By the irradiation of the skin, the IR radiation penetrates into the skin to a depth of about 50-100 μm and excites—depending on the wavelength—specific vibrations in the glucose molecule. These excitations from the vibration level v0 to v1 return to the basic state within a very short time; during this step heat is released.
4. As a result of the heat development according to (3), a thermal wave develops which propagates isotropically from the site of the absorption. Depending on the thermal diffusion length, determined by the low-frequency modulation described in (2), the thermal wave reaches the surface of the skin periodically at the modulation frequency.
5. The periodic appearance of the heat wave on the surface corresponds to a periodic modulation of the heat radiation characteristic of the skin (surface of the sample substance). The skin can be described here approximately as a black-body radiator, the total emission by the Stefan-Boltzmann law is proportional to the fourth power of the surface temperature.
6. A heat radiation detector, i.e. an infrared detector, i.e. a thermocouple, bolometer, semiconductor detector, piezo-detector or similar, directed at the point of irradiation on the skin, registers the periodic temperature rise described in (5). It depends on the irradiation of infrared light as described in (1) and (2) and on the absorption described in (3), and therefore depends on the concentration of glucose.

The heat radiation (in this case, the response signal) is collected, for example, by means of an optical element, in one embodiment an infrared lens or mirror, in particular a concave parabolic mirror, and in one embodiment is directed onto the detector via a convex mirror. For this purpose, a collecting mirror used in one embodiment can have an opening through which the collected beam is directed. In addition, a filter can be provided in the beam path that transmits only infrared radiation of a specific wavelength range.

In another exemplary embodiment, the heat radiation is detected by means of a measuring body, as claimed in the patent claims, by means of a piezoelectric effect.

7. In the processing of the response signals, the modulation frequency can be specifically taken into account, for which purpose the response signal can be processed in a lock-in amplifier. By analysing the phase offset between the excitation signal and the heat radiation signal (response signal) by means of a control and processing device, the depth information can be obtained via the depth below the surface of the substance from which the response signals are predominantly received.
8. The depth information can also be obtained by selecting and analysing different low-frequency modulation frequencies for the excitation beam as described in (2) and correlating the results for different modulation frequencies (wherein the results for different modulation frequencies can also be weighted differently). Differential methods, a quotient formation from at least two response signals in each case (for example, for a single wavelength and then passing by wavelengths through the measured spectrum) or other determination methods can be used to compensate for the absorption of the upper skin layers.
9. In order to make the detection of the heat radiation according to (6) as sensitive as possible, it is used as a broadband spectrum for the entire infrared range in question. As many regions of the Planck radiation curve as possible should be used. In order to render the detection insensitive to the intense excitation radiation, the detection of the heat radiation is provided with a blocking filter (notch filter) for these excitation wavelengths.
10. From the heat signal measured according to (6-9), which is dependent on the excitation wavelength, in one embodiment if glucose is to be detected, the background is thus determined initially at non-glucose-relevant (or excluding glucose-relevant) wavelengths of the excitation beam, and then at (or including) glucose-relevant wavelengths the difference relative to the background signal. This results in the glucose concentration in the skin layer or skin layers, which is determined by the selected phase offset according to (7) or the different modulation frequencies according to (8) or their correlation.

Although the invention has been illustrated and described in greater detail by means of preferred exemplary embodiments, the invention is not restricted by the examples disclosed and other variations can be derived therefrom by the person skilled in the art without departing from the scope of protection of the invention.

REFERENCE LIST 1 measuring body
1' layer
2 measuring surface
3 laser device
4 detection region
4' detection region
5 region, substance
5' position
6 contact device
6e-6y electrodes
7 surface normal
8 excitation beam
9 modulation device
10 region
11 flat body
12 mirror device
13 recess
14, 14a heat sink
15 thermal barrier
16 evaluation device
17-21 recesses
22-29 electrodes
32 conductor tracks
A direction, surface normal
B direction

The invention claimed is:
1. A device for analyzing a substance having:
a measuring body which has a measuring surface configured to be brought at least partially into contact with the substance for the measurement,
an excitation beam source for generating one or more excitation beams with different wavelengths configured to be directed at the substance while passing through the measuring surface, and
a detection device comprising:
a detection region which is part of the measuring body and arranged adjacent or directly adjacent to the measuring surface, and has electrical properties that vary as a function of a change in pressure or temperature, and electrodes configured to detect electrical signals representing the electrical properties, wherein at least two electrodes are arranged spaced apart from one another in a direction perpendicular to the surface normal of said measuring surface on different sides of the detection region.

2. The device for analyzing a substance according to claim 1, in which one or more of the electrical properties which vary as the function of the change in the pressure or temperature
gives rise to piezoelectric signals on the electrodes as a function of one or both of the pressure change and the temperature change, or
is formed by a specific electrical resistance, which varies according to the temperature,
wherein the detection device further comprises an electrical contact device which comprises the electrodes, which are electrically conductively connected to the detection region of the measuring body for detecting one or both of the electrical resistance and the piezoelectric signals.

3. The device for analyzing a substance according to claim 1, wherein at least two electrodes are arranged one behind the other at different distances from the measuring surface.

4. The device for analyzing a substance according to claim 1, wherein the one or more excitation beams pass through the measuring body, wherein an optical waveguide is arranged in or on the measuring body to guide the one or more excitation beams.

5. The device for analyzing a substance according to claim 1, wherein the one or more excitation beams pass through the measuring surface in a region directly adjacent to and/or adjoining the detection region.

6. The device for analyzing a substance according to claim 1, wherein a modulation device is provided for modulating an intensity of the one or more excitation beams.

7. The device for analyzing a substance according to claim 1, wherein at least three electrodes are arranged one behind another at different distances from the measuring surface, or spaced apart from each other in a direction perpendicular to a surface normal of the measuring surface.

8. The device for analyzing a substance according to claim 1, wherein at least three electrodes are arranged one behind another at different distances from the center of the detection region.

9. The device for analyzing a substance according to claim 1, wherein at least 6 electrodes are arranged in an annular region or a spherical shell-shaped region around the detection region and at least partially opposite one another on different sides of the detection region, different electrodes each being substantially the same distance from the center of the detection region or different distances from the center of the detection region.

10. The device for analyzing a substance according to claim 1, wherein one or more or all of the electrodes of the contact device are disc- or plate-shaped, annular, annular disc-shaped, in the form of a rectangular or polygonal frame with an opening, cap-shaped or rod-shaped.

11. The device for analyzing a substance according to claim 1, wherein one or more of the electrodes of the contact device are arranged on a surface of the measuring body or the detection device-.

12. The device for analyzing a substance according to claim 1, wherein one or more or all of the electrodes of the contact device are arranged on the inside of the measuring body or on an outer side thereof in one or more recesses of the measuring body.

13. The device for analyzing a substance according to claim 1, wherein the measuring body is formed as a flat body, wherein the thickness of the measuring body in the direction perpendicular to the measuring surface is less than 50% of the smallest extension of the measuring body in a direction extending in the measuring surface.

14. The device for analyzing a substance according to claim 13, wherein the measuring body has or carries a mirror device for reflecting the one or more excitation beams irradiated by the excitation beam source onto the measuring surface.

15. The device for analyzing a substance according to claim 1, wherein the one or more excitation beams are irradiated into the measuring body parallel to the measuring surface or at an angle of less than 30 degrees to the measuring surface, and wherein the one or more excitation beams are diverted or deflected in the direction of the measuring surface and passes through the measuring surface.

16. The device according to claim 1, wherein the one or more excitation beams pass through the material of the measuring body.

17. The device according to claim 1, wherein the measuring body has at least one recess or slot through which the one or more excitation beams pass, wherein the recess or slot extends from the measuring surface or from a sensor layer of the measuring body bounded by the measuring surface into the measuring body, or wherein the recess or slot penetrates the entire measuring body from a boundary surface of the measuring body opposite the measuring surface as far as the measuring surface.

18. The device according to claim 1, wherein in the measuring body, at least one heat sink is arranged in the form of a body, the specific thermal capacity and/or specific thermal conductivity of which is greater than the specific thermal capacity and/or specific thermal conductivity of the material or the materials from which the measuring body is made, or which is designed as a Peltier element.

19. The device according to claim 1, wherein in the measuring body, at least one thermal barrier is arranged in the form of a body, the specific thermal capacity or specific thermal conductivity of which is greater than the specific thermal capacity or specific thermal conductivity, respectively, of the material from which the measuring body is made.

20. The device according to claim 1, wherein one or more of the detection device, the measuring body and a sensor layer of the measuring body, is at least partially made of a piezoelectric material, wherein said piezoelectric material is one of a piezoelectric ceramic, and a mono-crystalline piezoelectric material.

21. The device of claim 20, wherein said piezoelectric material composition comprises one of quartz, tourmaline, lithium niobate, gallium orthophosphate, berlinite, Seignette salt, barium titanate (BTO), lead zirconate-titanate, gallium phosphate, a lead-magnesium niobate, zinc oxide (ZnO) or aluminium nitride as a thin-layer deposit, or polarized polyvinyl fluoride.

22. A method for operating a device according to claim 1, wherein a modulated excitation beam is directed, in particular through the measuring body, at the substance to be analyzed, and wherein signals from different electrode pairs of the detection device are acquired and evaluated simultaneously or sequentially, wherein it is firstly determined based on criteria which one or more of the pairs of electrodes delivers/deliver signals suitable for further processing, and wherein the signals from one or more selected electrode pairs are then used for measurement and evaluated, and wherein a subsequent measurement is performed in which the signals of the selected electrode pair or pairs are acquired and evaluated.

23. The method according to claim 22, wherein after an initial measurement test, depending on the signals detected a misalignment of the device relative to the substance to be analyzed is determined and indicated and, the user is prompted to perform a realignment.

24. A method for analyzing a substance, using a device according to claim 1, wherein the method comprises:
generating at least one intensity-modulated electromagnetic excitation beam with an excitation transmission device with at least one excitation wavelength, the excitation transmission device irradiates the at least one electromagnetic excitation beam into a volume of the substance which is located below a surface of the substance,
detecting a response signal using a detection device, and analyzing the substance on the basis of the detected response signal, wherein
successively determining response signals using different modulation frequencies of the excitation transmission device, including temporal response signal waveforms for different wavelengths of the at least one electromagnetic excitation beam, and
correlating a plurality of response signal waveforms at different modulation frequencies with one another and wherein
obtaining information specific to a depth range under the surface of the substance from the correlated response signal waveforms.

25. The device for analyzing a substance according to claim 1, further comprising an optical element for focusing the one or more excitation beams, wherein said optical element for focusing the one or more excitation beams is provided
between the excitation beam source and the measuring body,
on the measuring body where the one or more excitation beam enter the measuring body, or
on the measuring body in the region where the one or more excitation beams leave the measuring body.

26. The device of claim 1, wherein at least two electrodes are arranged spaced apart from one another on different sides of said excitation beam.

* * * * *